US007361807B2

(12) United States Patent
Zheng et al.

(10) Patent No.: US 7,361,807 B2
(45) Date of Patent: Apr. 22, 2008

(54) OAR POLYNUCLEOTIDES, POLYPEPTIDES AND THEIR USE IN PHA PRODUCTION IN PLANTS

(75) Inventors: Peizhong Zheng, Johnston, IA (US); Chun Ping Li, Johnston, IA (US); Scott E. Nichols, Westchester, PA (US)

(73) Assignee: Pioneer Hi-Bred International. Inc., Des Moines, IA (US)

( * ) Notice: Subject to any disclaimer, the term of this patent is extended or adjusted under 35 U.S.C. 154(b) by 0 days.

(21) Appl. No.: 11/521,157

(22) Filed: Sep. 14, 2006

(65) Prior Publication Data

US 2007/0011771 A1 Jan. 11, 2007

Related U.S. Application Data

(62) Division of application No. 10/926,499, filed on Aug. 26, 2004, now Pat. No. 7,129,395, which is a division of application No. 10/024,806, filed on Dec. 19, 2001, now Pat. No. 6,806,401.

(60) Provisional application No. 60/258,417, filed on Dec. 27, 2000.

(51) Int. Cl.
*C12P 7/62* (2006.01)
*C12P 11/00* (2006.01)
*C07H 21/04* (2006.01)
*A01H 1/00* (2006.01)

(52) U.S. Cl. ............... 800/295; 435/69.1; 435/468; 435/320.1; 435/410; 435/419; 435/6; 435/183; 435/135; 530/350; 530/370; 536/23.1; 536/23.2; 536/23.6; 800/278; 800/281; 800/284

(58) Field of Classification Search .................. None
See application file for complete search history.

(56) References Cited

U.S. PATENT DOCUMENTS

| 4,956,282 | A | 9/1990 | Goodman et al. |
| 5,245,023 | A | 9/1993 | Peoples et al. |
| 5,650,555 | A | 7/1997 | Somerville et al. |
| 6,143,952 | A | 11/2000 | Srienc et al. |
| 6,346,395 | B1 | 2/2002 | Chalker et al. |

FOREIGN PATENT DOCUMENTS

| WO | WO-98/00557 A2 | 1/1998 |
| WO | WO-99/00505 A1 | 1/1999 |
| WO | WO-99/35278 A1 | 7/1999 |
| WO | WO-99/45122 A1 | 9/1999 |
| WO | WO-00/55328 A1 | 9/2000 |

OTHER PUBLICATIONS

Klein, et al. (Feb. 16, 1992) PIR_80 Database. Accession No. S22450 (U), Mol. Gen. Genet. 233:122-128(1992).*
Klein, et al. (Feb. 16, 1992) UniProt_8.4 Database. Accession No. FABG_CUPLA (V), Mol. Gen. Genet. 233:122-128(1992).*

Caughey, I., and R. Kekwick, "The Characteristics of Some Components of the Fatty Acid Synthetase System in the Plastids from the Mesocarp of Avocado (*Persea americana*) Fruit," *Eur. J. Biochem.*, 1982, pp. 553-561, vol. 123, FEBS.
Fukui, T., et al., "Expression and Characterization of (*R*)-Specific Enoyl Coenzyme A Hydratase Involved in Polyhydroxyalkanoate Biosynthesis by *Aeromonas caviae*," *Journal of Bacteriology*, Feb. 1998, pp. 667-673, vol. 180(3), American Society for Microbiology, USA.
Hashimoto, T., "Peroxisomal β-Oxidation Enzymes," *Neurochemical Research*, 1999, pp. 551-563, vol. 24(4), Plenum Publishing Corporation.
Hiltunen, J., et al., "Peroxisomal Multifunctional β-Oxidation Protein of *Saccharomyces-cerevisiaes*: Molecular Analysis of the Fox2 Gene and Gene Product," *The Journal of Biological Chemistry*, Apr. 1992, pp. 6646-6653, vol. 267(10),. The American Society for Biochemistry and Molecular Biology, Inc., USA.
Jiang, L., et al., "Purification and Properties of Rat D-3 Hydroxyacyl-CoA Dehydratase: D-3-Hydroxyacyl-CoA Dehydratase/D-3-Hydroxyacyl-CoA Dehydrogenase Bifunctional Protein," *J. Biochem*, Sep. 1996, pp. 633-641, vol. 120(3), the Japanese Biochemical Society, Japan.
Kato, M., et al., "Production of a Novel Copolyester of 3-hydroxybutyric Acid and Medium-Chain-Length 3-Hydroxyalkanoic Acids by *Pseudomonas* sp. 61-3 from Sugars," *Appl. Microbiol. Biotechnol.*, 1996, pp. 363-370, vol. 45, Springer-Verlag.
Klein, B., et al., "Isolation and Characterization of cDNA from *Cuphea lanceolata* Encoding a β-Ketoacyl-ACP Reductase," *Mol. Gen. Genet.*, 1992, pp. 122-128, vol. 233.
Lee, E., et al., "Biosynthesis of Copolyesters Consisting of 3-hydroxybutyric Acid and Medium-Chain-Length 3-Hydroxyalkanoic Acids from 1,3-Butanediol or from 3-Hydroxybutyrate by *Pseudomonas* sp. A33," *Appl. Microbiol. Biotechnol.*, 1995, pp. 901-909, vol. 42, Springer-Verlag.
Liebergesell, M., et al., "Analysis of Polyhydroxyalkanoic Acid-Biosynthesis Genes of Anoxygenic Phototrophic Bacteria Reveals Synthesis of a Polyester Exhibiting an Unusual Composition," *Appl. Microbiol. Biotechnol.*, 1993, pp. 292-300, vol. 40, Springer-Verlag.
Madison, L. and B. Huisman, "Metabolic Engineering of Poly(3-Hydroxyalkanoates): From DNA to Plastic," *Microbiology and Molecular Biology Reviews*, Mar. 1999, pp. 21-53, vol. 63(1), American Society for Microbiology, USA.
Matsusaki, H., et al., "Cloning and Molecular Analysis of the Poly(3-Hydroxybutyrate) and Poly(3-Hydroxybutyrate-*co*-3-Hydroxyalkanoate) Biosynthesis Genes in *Pseudomonas* sp. Strain 61-3," *Journal of Bacteriology*, Dec. 1998, pp. 6459-6467, vol. 180(24), American Society for Microbiology, USA.

(Continued)

*Primary Examiner*—Phuong T. Bui
*Assistant Examiner*—Brendan O. Baggot
(74) *Attorney, Agent, or Firm*—Alston & Bird LLP

(57) ABSTRACT

The invention relates to the genes encoding 3-oxoacyl-[acyl carrier protein(ACP)] reductase (OAR). Compositions and methods for producing polyhydroxyalkanoate in transformed plants and transformed host cells are provided. Such methods find use in producing biodegradable thermoplastics in host cells and plants. Isolated nucleotide molecules, expression cassettes, isolated polypeptides and genetically manipulated host cells, plants, plant tissues, plant cells and seeds are also provided.

19 Claims, No Drawings

OTHER PUBLICATIONS

Mittendorf, V., et al., "Synthesis of Medium-Chain-Length Polyhydroxyalkanoates in *Arabidopsis Thaliana* Using Intermediates of Peroxisomal Fatty Acid β-Oxidation," *Proc. Natl. Acad. Sci. USA*, Nov. 1998, pp. 13397-13402, vol. 95, The National Academy of Sciences.

Nishiyama, M., et al., "Alteration of Coenzyme Specificity of Malate Dehydrogenase from *Thermus flavus* by Site-directed Mutagenesis," *The Journal of Biological Chemistry*, Mar. 1993, pp. 4656-4660, vol. 268(7), The American Society for Biochemistry and Molecular Biology, Inc., USA.

Poirier, Y., "Production of New Polymeric Compounds in Plants," *Current Opinion in Biotechnology*, Apr. 1999, pp. 181-185, vol. 10(2), Elsevier Science Ltd.

Solaiman, D., "PCR Cloining of *Pseudomonas resinovorans* Polyhydroxyalkanoate Biosynthesis Genes and Expression in *Escherichia coli*," *Biotechnology Letters*, 2000, pp. 789-794, vol. 22, Kluwer Academic Publishers, Netherlands.

Shimakata, T., and P. Stumpf, "Purification and Characterizations of β-Ketoacyl-[Acyl-Carrier-Protein] Reductase, β-Hydroxyacyl-[Acyl-Carrier-Protein] Dehydrase, and Enoyl—[Acyl-Carrier-Protein] Reductase from *Spinacia oleracea* Leaves," *Archives of Biochemistry and Biophysics*, Oct. 1982, pp. 77-91, vol. 218(1), Academic Press, Inc.

Taguchi, K., et al., "Co-Expression of 3-Ketoacyl-ACP Reductase and Polyhydroxyalkanoate Synthase Genes Induces PHA Production in *Escherichia coli* HB101 Strain," *FEMS Microbiology Letters* 1999, pp. 183-190, vol. 176, Elsevier Science B.V.

Timm, A., and A. Steinbüchel, "Cloning and Molecular Analysis of the Poly(3-Hydroxyalkanoic Acid) Gene Locus of *Pseudomonas aeruginosa* PAO1," *Eur. J. Biochem.*, 1992, pp. 15-30, vol. 209, FEBS.

Williams, M., et al., "Production of a Polyhydroxyalkanoate Biopolymer in Insect Cells with a Modified Eucaryotic Fatty Acid Synthase," *Applied and Environmental Microbiology*, Jul. 1996, pp. 2540-2546, vol. 62(7), American Society for Microbiology, USA.

EMBL Database Report for Accession No. AF129396, Apr. 26, 1999 (XP-002167125).

EMBL Database Report for Accession No. AI657354, May 6, 1999 (XP-002167910).

EMBL Database Report for Accession No. BE056943, Jun. 20, 2000 (XP-002167911).

\* cited by examiner

SEQUENCE LISTING

```
<160> NUMBER OF SEQ ID NOS: 10

<210> SEQ ID NO 1
<211> LENGTH: 1326
<212> TYPE: DNA
<213> ORGANISM: Zea mays
<220> FEATURE:
<221> NAME/KEY: CDS
<222> LOCATION: (157)...(1110)

<400> SEQUENCE: 1
gcgcggagct tccaaagccc ccgtccccca atagactcct ccccatccgt gctctgctcc        60
gtcacggctc aaatactccg cctgcatctc caaagcacac tgctccctct ggcttcccgc       120
ctcctcttcg gctccttcgc gtcccgacgc ccccte atg gcc acc gcc gcc gcc        174
                                        Met Ala Thr Ala Ala Ala
                                        1               5 acc gca gca gca gca gca gtc tcc tcc ccg gct gcg cgt gga gca gcc        222
Thr Ala Ala Ala Ala Ala Val Ser Ser Pro Ala Ala Arg Gly Ala Ala
            10                  15                  20 ggg gcc gcc gcc gcc tcc cgc cgg ggg ttc gtc acg ttt ggt gga ggc        270
Gly Ala Ala Ala Ala Ser Arg Arg Gly Phe Val Thr Phe Gly Gly Gly
        25                  30                  35 gcc gcc cgc ttc tct ccc acg ctg cgg tcc ggc cgt ggg ttc tct ggt        318
Ala Ala Arg Phe Ser Pro Thr Leu Arg Ser Gly Arg Gly Phe Ser Gly
    40                  45                  50 gtg caa acc cat gtt gct gct gtt gaa caa gca gtt gta aaa gat gct        366
Val Gln Thr His Val Ala Ala Val Glu Gln Ala Val Val Lys Asp Ala
```

```
                                                      -continued
          55                  60                  65                  70
acc aag ctg gaa gct cca gtt gtt gtt gtt aca ggt gca tct aga ggg        414
Thr Lys Leu Glu Ala Pro Val Val Val Val Thr Gly Ala Ser Arg Gly
                    75                  80                  85 att ggt aag gca act gct cta gcc ctt gga aaa gca gga tgc aag gtt        462
Ile Gly Lys Ala Thr Ala Leu Ala Leu Gly Lys Ala Gly Cys Lys Val
            90                  95                 100 ctg gta aac tat gcc cgg tcc tcg aaa gag gct gaa gag gtc tcc aaa        510
Leu Val Asn Tyr Ala Arg Ser Ser Lys Glu Ala Glu Glu Val Ser Lys
           105                 110                 115 gag att gaa gca tct ggt ggt gag gct atc acc ttc gga gga gat gtt        558
Glu Ile Glu Ala Ser Gly Gly Glu Ala Ile Thr Phe Gly Gly Asp Val
       120                 125                 130 tca aaa gaa gct gat gta gag tct atg atg aaa gca gct cta gat aaa        606
Ser Lys Glu Ala Asp Val Glu Ser Met Met Lys Ala Ala Leu Asp Lys
135                 140                 145                 150 tgg gga aca ata gat gtg ctg gta aat aat gca ggg att aca cga gac        654
Trp Gly Thr Ile Asp Val Leu Val Asn Asn Ala Gly Ile Thr Arg Asp
                155                 160                 165 aca ttg ttg atg agg atg aag aaa tct cag tgg caa gac gta att gat        702
Thr Leu Leu Met Arg Met Lys Lys Ser Gln Trp Gln Asp Val Ile Asp
            170                 175                 180 ctg aat ctt act ggc gtc ttc ctt tgt aca cag gct gca aca aaa gta        750
Leu Asn Leu Thr Gly Val Phe Leu Cys Thr Gln Ala Ala Thr Lys Val
        185                 190                 195 atg atg aaa aag aga aag gga aaa att atc aac att gca tct gta gtt        798
Met Met Lys Lys Arg Lys Gly Lys Ile Ile Asn Ile Ala Ser Val Val
    200                 205                 210 ggt ctt act ggc aat gtt ggc caa gct aat tat agc gca gcc aag gct        846
Gly Leu Thr Gly Asn Val Gly Gln Ala Asn Tyr Ser Ala Ala Lys Ala
215                 220                 225                 230 gga gtg att ggt ttc aca aaa aca gtt gcc agg gag tat gca agc aga        894
Gly Val Ile Gly Phe Thr Lys Thr Val Ala Arg Glu Tyr Ala Ser Arg
                235                 240                 245 aat atc aat gtg aat gct att gca cca ggg ttc att gca tct gat atg        942
Asn Ile Asn Val Asn Ala Ile Ala Pro Gly Phe Ile Ala Ser Asp Met
            250                 255                 260 act gcc gaa ctt gga gaa gag ctt gag aag aaa atc ttg tca acc att        990
Thr Ala Glu Leu Gly Glu Glu Leu Glu Lys Lys Ile Leu Ser Thr Ile
        265                 270                 275 ccg tta ggg aga tat ggc caa cca gag gaa gtt gca ggg ttg gtc gag       1038
Pro Leu Gly Arg Tyr Gly Gln Pro Glu Glu Val Ala Gly Leu Val Glu
    280                 285                 290 ttc ctg gcc ctt aac ccc gca gct agc tat atg act gga cag gtg ctt       1086
Phe Leu Ala Leu Asn Pro Ala Ala Ser Tyr Met Thr Gly Gln Val Leu
295                 300                 305                 310 aca att gac gga ggg atg gta atg taagatttga gttagcttga tgcacttcta      1140
Thr Ile Asp Gly Gly Met Val Met
                315 cttttgctga gcatttaatg ttgaacaccc ttgttgtgca cgggcgattt tggacaacaa     1200 attagtgttg tctctttctt tgtaatactc tctggtaata aatctagcat gtggaatgga     1260 agttgaaatc tgggttttcg tgtaaaaaaa aaaaaaaaaa aaaaaaaaaa aaaaaaaaaa     1320 aaaaaa                                                               1326

<210> SEQ ID NO 2
<211> LENGTH: 318
<212> TYPE: PRT
<213> ORGANISM: Zea mays
```

<400> SEQUENCE: 2

```
Met Ala Thr Ala Ala Thr Ala Ala Ala Ala Val Ser Ser Pro
  1               5                  10                  15
Ala Ala Arg Gly Ala Ala Gly Ala Ala Ala Ser Arg Arg Gly Phe
             20                  25                  30
Val Thr Phe Gly Gly Gly Ala Ala Arg Phe Ser Pro Thr Leu Arg Ser
             35                  40                  45
Gly Arg Gly Phe Ser Gly Val Gln Thr His Val Ala Ala Val Glu Gln
             50                  55                  60
Ala Val Val Lys Asp Ala Thr Lys Leu Glu Ala Pro Val Val Val
 65              70                  75                  80
Thr Gly Ala Ser Arg Gly Ile Gly Lys Ala Thr Ala Leu Ala Leu Gly
                 85                  90                  95
Lys Ala Gly Cys Lys Val Leu Val Asn Tyr Ala Arg Ser Ser Lys Glu
                100                 105                 110
Ala Glu Glu Val Ser Lys Glu Ile Glu Ala Ser Gly Gly Glu Ala Ile
                115                 120                 125
Thr Phe Gly Gly Asp Val Ser Lys Glu Ala Asp Val Glu Ser Met Met
                130                 135                 140
Lys Ala Ala Leu Asp Lys Trp Gly Thr Ile Asp Val Leu Val Asn Asn
145                 150                 155                 160
Ala Gly Ile Thr Arg Asp Thr Leu Leu Met Arg Met Lys Lys Ser Gln
                165                 170                 175
Trp Gln Asp Val Ile Asp Leu Asn Leu Thr Gly Val Phe Leu Cys Thr
                180                 185                 190
Gln Ala Ala Thr Lys Val Met Met Lys Lys Arg Lys Gly Lys Ile Ile
                195                 200                 205
Asn Ile Ala Ser Val Val Gly Leu Thr Gly Asn Val Gly Gln Ala Asn
                210                 215                 220
Tyr Ser Ala Ala Lys Ala Gly Val Ile Gly Phe Thr Lys Thr Val Ala
225                 230                 235                 240
Arg Glu Tyr Ala Ser Arg Asn Ile Asn Val Asn Ala Ile Ala Pro Gly
                245                 250                 255
Phe Ile Ala Ser Asp Met Thr Ala Glu Leu Gly Glu Glu Leu Glu Lys
                260                 265                 270
Lys Ile Leu Ser Thr Ile Pro Leu Gly Arg Tyr Gly Gln Pro Glu Glu
                275                 280                 285
Val Ala Gly Leu Val Glu Phe Leu Ala Leu Asn Pro Ala Ala Ser Tyr
                290                 295                 300
Met Thr Gly Gln Val Leu Thr Ile Asp Gly Gly Met Val Met
305                 310                 315
```

<210> SEQ ID NO 3
<211> LENGTH: 1286
<212> TYPE: DNA
<213> ORGANISM: Zea mays
<220> FEATURE:
<221> NAME/KEY: CDS
<222> LOCATION: (115)...(1050)

<400> SEQUENCE: 3

```
ccacaccaaa cgtgccaaac ccccaacgcc atcctctata aacggcttcc tcgcgggctc      60
cccctccccc tcccgactc ctcccatcg cccatcgccg ccctccgatc cttc atg        117
                                                            Met
                                                            1
```

```
gcc gct gcc aca gcc gcc gcc gcg ctc gcc tcc ccg gcg ggc ctc      165
Ala Ala Ala Thr Ala Ala Ala Ala Leu Ala Ser Pro Ala Gly Leu
            5                  10                  15 tcc aca tcg ctg gcg cgc cgc ggc ctc gtc agc ttc gca ccc gcg ctc  213
Ser Thr Ser Leu Ala Arg Arg Gly Leu Val Ser Phe Ala Pro Ala Leu
        20                  25                  30 cgc ccc ggc cct gac cgc agc tct cgc gcc gtc gcc ctc ctc ggt gta  261
Arg Pro Gly Pro Asp Arg Ser Ser Arg Ala Val Ala Leu Leu Gly Val
    35                  40                  45 cga act cat gtc acg gct gtt gat caa gcc att gta aaa ggt gat aca  309
Arg Thr His Val Thr Ala Val Asp Gln Ala Ile Val Lys Gly Asp Thr
50                  55                  60                  65 aag ttg gaa ggt cct gtg gtt gtt gtt act ggt gct tcc agg ggg att  357
Lys Leu Glu Gly Pro Val Val Val Val Thr Gly Ala Ser Arg Gly Ile
                70                  75                  80 gga aaa gcc act gca ttg gct ctt gga aaa gca ggc tgc aag gtc ttg  405
Gly Lys Ala Thr Ala Leu Ala Leu Gly Lys Ala Gly Cys Lys Val Leu
            85                  90                  95 gtg aat tat gct cga tct tca aag gag gct gaa gaa gtc tcc aag gag  453
Val Asn Tyr Ala Arg Ser Ser Lys Glu Ala Glu Glu Val Ser Lys Glu
        100                 105                 110 att gaa gca tct gga ggc cag gcc att acc ttt gga gga gat gtt tcc  501
Ile Glu Ala Ser Gly Gly Gln Ala Ile Thr Phe Gly Gly Asp Val Ser
    115                 120                 125 aaa gag gct gat gtt gaa tct atg ata aaa gtg gct gtt gat aca tgg  549
Lys Glu Ala Asp Val Glu Ser Met Ile Lys Val Ala Val Asp Thr Trp
130                 135                 140                 145 gga acg att gat gta cta gta aat aat gca gga atc aca cgg gac aca  597
Gly Thr Ile Asp Val Leu Val Asn Asn Ala Gly Ile Thr Arg Asp Thr
                150                 155                 160 ttg ttg atg aga atg aag aaa tca cag tgg caa gat gcg att gat ttg  645
Leu Leu Met Arg Met Lys Lys Ser Gln Trp Gln Asp Ala Ile Asp Leu
            165                 170                 175 aat ctt aca ggc gtt ttc ctt tgc acg cag gct gca aca aaa gta atg  693
Asn Leu Thr Gly Val Phe Leu Cys Thr Gln Ala Ala Thr Lys Val Met
        180                 185                 190 atg aag aag aaa aag gga aga att atc aat ata gca tcg gtt gtt ggt  741
Met Lys Lys Lys Lys Gly Arg Ile Ile Asn Ile Ala Ser Val Val Gly
    195                 200                 205 ctt act ggt aat gct gga caa gct aat tat gct gct gcc aag gct ggg  789
Leu Thr Gly Asn Ala Gly Gln Ala Asn Tyr Ala Ala Ala Lys Ala Gly
210                 215                 220                 225 gtt att ggg ttc aca aaa aca gtt gct agg gag tat gcc agc aga aat  837
Val Ile Gly Phe Thr Lys Thr Val Ala Arg Glu Tyr Ala Ser Arg Asn
                230                 235                 240 att aat gca aac gtt atc gct cct gga ttt att gct tca gat atg act  885
Ile Asn Ala Asn Val Ile Ala Pro Gly Phe Ile Ala Ser Asp Met Thr
            245                 250                 255 gct gaa ctt ggt gaa gag tta gag aag aaa att ctg tca act att cct  933
Ala Glu Leu Gly Glu Glu Leu Glu Lys Lys Ile Leu Ser Thr Ile Pro
        260                 265                 270 tta ggg cgc tat ggt cgg cca gag gat gta gca ggc ctg gtg gaa ttc  981
Leu Gly Arg Tyr Gly Arg Pro Glu Asp Val Ala Gly Leu Val Glu Phe
    275                 280                 285 tta gcc ctc agc cct gct gca agc tac atc act gga cag gtc ctc acc  1029
Leu Ala Leu Ser Pro Ala Ala Ser Tyr Ile Thr Gly Gln Val Leu Thr
290                 295                 300                 305 atc gat gga gga atg gta atg taaggcttcg aatctgtgcc gctggcctct     1080
Ile Asp Gly Gly Met Val Met
```

```
aatgtgtcgc agaaaaaaaa tgtaattcag ttttttgagt gtcattttta agggtggtt    1140 tcttttgtcc gcagcggttt gtggtatagt acagtttgtt tcgaagggag agttgatact   1200
agaaatttgc acacgtatag ttagcttaat ttctttgcga ttggccgatt gctccaaaaa   1260
aaaaaaaaaa aaaaaaaaaa aaaaaa                                       1286
```

<210> SEQ ID NO 4
<211> LENGTH: 312
<212> TYPE: PRT
<213> ORGANISM: Zea mays

<400> SEQUENCE: 4

```
Met Ala Ala Thr Ala Ala Ala Ala Leu Ala Ser Pro Ala Gly
 1               5                  10                  15

Leu Ser Thr Ser Leu Ala Arg Arg Gly Leu Val Ser Phe Ala Pro Ala
            20                  25                  30

Leu Arg Pro Gly Pro Asp Arg Ser Arg Ala Val Ala Leu Leu Gly
        35                  40                  45

Val Arg Thr His Val Thr Ala Val Asp Gln Ala Ile Val Lys Gly Asp
 50                  55                  60

Thr Lys Leu Glu Gly Pro Val Val Val Thr Gly Ala Ser Arg Gly
65                  70                  75                  80

Ile Gly Lys Ala Thr Ala Leu Ala Leu Gly Lys Ala Gly Cys Lys Val
                85                  90                  95

Leu Val Asn Tyr Ala Arg Ser Ser Lys Glu Ala Glu Val Ser Lys
            100                 105                 110

Glu Ile Glu Ala Ser Gly Gly Gln Ala Ile Thr Phe Gly Gly Asp Val
        115                 120                 125

Ser Lys Glu Ala Asp Val Glu Ser Met Ile Lys Val Ala Val Asp Thr
130                 135                 140

Trp Gly Thr Ile Asp Val Leu Val Asn Asn Ala Gly Ile Thr Arg Asp
145                 150                 155                 160

Thr Leu Leu Met Arg Met Lys Lys Ser Gln Trp Gln Asp Ala Ile Asp
                165                 170                 175

Leu Asn Leu Thr Gly Val Phe Leu Cys Thr Gln Ala Thr Lys Val
            180                 185                 190

Met Met Lys Lys Lys Gly Arg Ile Ile Asn Ile Ala Ser Val Val
        195                 200                 205

Gly Leu Thr Gly Asn Ala Gly Gln Ala Asn Tyr Ala Ala Ala Lys Ala
        210                 215                 220

Gly Val Ile Gly Phe Thr Lys Thr Val Ala Arg Glu Tyr Ala Ser Arg
225                 230                 235                 240

Asn Ile Asn Ala Asn Val Ile Ala Pro Gly Phe Ile Ala Ser Asp Met
                245                 250                 255

Thr Ala Glu Leu Gly Glu Glu Leu Glu Lys Lys Ile Leu Ser Thr Ile
            260                 265                 270

Pro Leu Gly Arg Tyr Gly Arg Pro Glu Asp Val Ala Gly Leu Val Glu
        275                 280                 285

Phe Leu Ala Leu Ser Pro Ala Ala Ser Tyr Ile Thr Gly Gln Val Leu
    290                 295                 300

Thr Ile Asp Gly Gly Met Val Met
305                 310
```

-continued

```
<210> SEQ ID NO 5
<211> LENGTH: 1398
<212> TYPE: DNA
<213> ORGANISM: Glycine max
<220> FEATURE:
<221> NAME/KEY: CDS
<222> LOCATION: (122)...(1081)

<400> SEQUENCE: 5
cccaaagcac taatctaaca aacgcaattt aaaaaccgca acaaactttc tctcttgcgt      60
tcacacttat tctctggctt cttcttccat tttcgcttct cgtagcgttt tcggaacagt     120 t atg gct tcc att gcc gga tcc aac tgc gtc gct ctc cga acc gcc aac    169
  Met Ala Ser Ile Ala Gly Ser Asn Cys Val Ala Leu Arg Thr Ala Asn
   1               5                   10                  15 ttc ggc gcc tcc ggt aac cgg aaa atc ggc cag atc cgc caa tgg tct       217
Phe Gly Ala Ser Gly Asn Arg Lys Ile Gly Gln Ile Arg Gln Trp Ser
                20                  25                  30 ccg att ctc acg aat ctc cgt ccc gtt tcc ggt ctt cgt cac cga tcg       265
Pro Ile Leu Thr Asn Leu Arg Pro Val Ser Gly Leu Arg His Arg Ser
             35                  40                  45 aat act ccg ttt agc tcc tcc ggt gtg aga gca cag gtt gct act ctg       313
Asn Thr Pro Phe Ser Ser Ser Gly Val Arg Ala Gln Val Ala Thr Leu
         50                  55                  60 gag gaa gca gga acc gga gca act cag aaa gtg gaa gcg ccg gtt gca       361
Glu Glu Ala Gly Thr Gly Ala Thr Gln Lys Val Glu Ala Pro Val Ala
 65                  70                  75                  80 gtg gtg acc gga gct tcc aga ggc att ggc aaa gcg att gca ctg tca       409
Val Val Thr Gly Ala Ser Arg Gly Ile Gly Lys Ala Ile Ala Leu Ser
                 85                  90                  95 tta ggt aaa gca ggt tgc aag gtt ctg gtc aac tat gca agg tca tcc       457
Leu Gly Lys Ala Gly Cys Lys Val Leu Val Asn Tyr Ala Arg Ser Ser
            100                 105                 110 aag gaa gct gag gag gtt tcc aag gag att gag gag ttt ggt ggt caa       505
Lys Glu Ala Glu Glu Val Ser Lys Glu Ile Glu Glu Phe Gly Gly Gln
        115                 120                 125 gct ctt aca ttt ggt gga gat gtt tct aac gag gct gat gtg gag tct       553
Ala Leu Thr Phe Gly Gly Asp Val Ser Asn Glu Ala Asp Val Glu Ser
    130                 135                 140 atg att aaa act gca gtt gat gct tgg gga aca gtt gat gta tta ata       601
Met Ile Lys Thr Ala Val Asp Ala Trp Gly Thr Val Asp Val Leu Ile
145                 150                 155                 160 aac aat gca gga ata aca aga gat ggt tta tta atg aga atg aag aaa       649
Asn Asn Ala Gly Ile Thr Arg Asp Gly Leu Leu Met Arg Met Lys Lys
                165                 170                 175 tct caa tgg cag gat gtt att gat cta aat ctc act ggt gtt ttt ctt       697
Ser Gln Trp Gln Asp Val Ile Asp Leu Asn Leu Thr Gly Val Phe Leu
            180                 185                 190 tgc aca cag gct gct gct aag att atg atg aag aaa aag aag gga agg       745
Cys Thr Gln Ala Ala Ala Lys Ile Met Met Lys Lys Lys Lys Gly Arg
        195                 200                 205 atc gtc aat att gca tca gtt gtt ggt ttg gtt ggc aat gtt gga caa       793
Ile Val Asn Ile Ala Ser Val Val Gly Leu Val Gly Asn Val Gly Gln
    210                 215                 220 gcc aat tat agt gct gca aaa gca gga gta att ggc ctg aca aaa act       841
Ala Asn Tyr Ser Ala Ala Lys Ala Gly Val Ile Gly Leu Thr Lys Thr
225                 230                 235                 240 gtt gcg aag gaa tat gct agt aga aac atc act gtt aat gca gtt gct       889
Val Ala Lys Glu Tyr Ala Ser Arg Asn Ile Thr Val Asn Ala Val Ala
                245                 250                 255 cca ggg ttt att gca tct gac atg act gcc aag cta gga caa gac att       937
Pro Gly Phe Ile Ala Ser Asp Met Thr Ala Lys Leu Gly Gln Asp Ile
```

-continued

```
Pro Gly Phe Ile Ala Ser Asp Met Thr Ala Lys Leu Gly Gln Asp Ile
            260                 265                 270 gag aaa aag att ttg gag aca atc cca tta gga aga tat ggc caa cca      985
Glu Lys Lys Ile Leu Glu Thr Ile Pro Leu Gly Arg Tyr Gly Gln Pro
        275                 280                 285 gag gaa gtt gct gga ctg gtt gaa ttc ttg gct ctt aat caa gct gcc     1033
Glu Glu Val Ala Gly Leu Val Glu Phe Leu Ala Leu Asn Gln Ala Ala
    290                 295                 300 agt tac atc act ggg cag gtt ttc acc att gat gga ggt atg gtg atg     1081
Ser Tyr Ile Thr Gly Gln Val Phe Thr Ile Asp Gly Gly Met Val Met
305                 310                 315                 320 taaattagca atccttttac cttgcaacat gagcttttgc acttttaaac tacttctgta   1141
cggtgatagt ttgttctttg ctgagttttg tttaagctag ttttaccctg tgatttatcg   1201
tagaatatta gttgaaatgc aattcagtca cttttggcac tagctctgaa ttgcttactg   1261
atgaaatgca atgtgtccag catcttgtac cattttggtt tttatggtca tgtcagaga   1321 ataggcataa ttcttatatg caattcagtc acttttggca ctaaaaaaaa aaaaaaaaaa   1381
aaaaaaaaaa aaaaaa                                                   1398

<210> SEQ ID NO 6
<211> LENGTH: 320
<212> TYPE: PRT
<213> ORGANISM: Glycine max

<400> SEQUENCE: 6

Met Ala Ser Ile Ala Gly Ser Asn Cys Val Ala Leu Arg Thr Ala Asn
 1               5                  10                  15

Phe Gly Ala Ser Gly Asn Arg Lys Ile Gly Gln Ile Arg Gln Trp Ser
            20                  25                  30

Pro Ile Leu Thr Asn Leu Arg Pro Val Ser Gly Leu Arg His Arg Ser
        35                  40                  45

Asn Thr Pro Phe Ser Ser Ser Gly Val Arg Ala Gln Val Ala Thr Leu
    50                  55                  60

Glu Glu Ala Gly Thr Gly Ala Thr Gln Lys Val Glu Ala Pro Val Ala
65                  70                  75                  80

Val Val Thr Gly Ala Ser Arg Gly Ile Gly Lys Ala Ile Ala Leu Ser
                85                  90                  95

Leu Gly Lys Ala Gly Cys Lys Val Leu Val Asn Tyr Ala Arg Ser Ser
            100                 105                 110

Lys Glu Ala Glu Glu Val Ser Lys Glu Ile Glu Phe Gly Gly Gln
            115                 120                 125

Ala Leu Thr Phe Gly Gly Asp Val Ser Asn Glu Ala Asp Val Glu Ser
    130                 135                 140

Met Ile Lys Thr Ala Val Asp Ala Trp Gly Thr Val Asp Val Leu Ile
145                 150                 155                 160

Asn Asn Ala Gly Ile Thr Arg Asp Gly Leu Leu Met Arg Met Lys Lys
                165                 170                 175

Ser Gln Trp Gln Asp Val Ile Asp Leu Asn Leu Thr Gly Val Phe Leu
            180                 185                 190

Cys Thr Gln Ala Ala Ala Lys Ile Met Met Lys Lys Lys Gly Arg
        195                 200                 205

Ile Val Asn Ile Ala Ser Val Val Gly Leu Val Gly Asn Val Gly Gln
    210                 215                 220

Ala Asn Tyr Ser Ala Ala Lys Ala Gly Val Ile Gly Leu Thr Lys Thr
225                 230                 235                 240
```

```
Val Ala Lys Glu Tyr Ala Ser Arg Asn Ile Thr Val Asn Ala Val Ala
                245                 250                 255

Pro Gly Phe Ile Ala Ser Asp Met Thr Ala Lys Leu Gly Gln Asp Ile
            260                 265                 270

Glu Lys Lys Ile Leu Glu Thr Ile Pro Leu Gly Arg Tyr Gly Gln Pro
        275                 280                 285

Glu Glu Val Ala Gly Leu Val Glu Phe Leu Ala Leu Asn Gln Ala Ala
    290                 295                 300

Ser Tyr Ile Thr Gly Gln Val Phe Thr Ile Asp Gly Gly Met Val Met
305                 310                 315                 320

<210> SEQ ID NO 7
<211> LENGTH: 1248
<212> TYPE: DNA
<213> ORGANISM: Glycine max
<220> FEATURE:
<221> NAME/KEY: CDS
<222> LOCATION: (16)...(912)

<400> SEQUENCE: 7
```

| | | |
|---|---|---|
| cagaaatcaa gtaag atg ggt tct ctg gcc cga cca aac tca ctc ttt ttt<br>                        Met Gly Ser Leu Ala Arg Pro Asn Ser Leu Phe Phe<br>                         1             5                   10 | 51 |
| cga acc aaa gga ccc gga cgt gcc cgg aaa gta cca agt cag gtt ttg<br>Arg Thr Lys Gly Pro Gly Arg Ala Arg Lys Val Pro Ser Gln Val Leu<br>       15                  20                25 | 99 |
| gct ttt cag cgt tcc aat tca aat ggt tca ttt ccc tca tca gaa cag<br>Ala Phe Gln Arg Ser Asn Ser Asn Gly Ser Phe Pro Ser Ser Glu Gln<br>   30                  35               40 | 147 |
| cta gaa ctt gaa gca agc cag aag aac atg gaa gca cct gtt gtt gta<br>Leu Glu Leu Glu Ala Ser Gln Lys Asn Met Glu Ala Pro Val Val Val<br> 45                50               55                60 | 195 |
| gtc act gga gcc tcc aga ggc att ggc cgt gca att gca ctt tcc ttg<br>Val Thr Gly Ala Ser Arg Gly Ile Gly Arg Ala Ile Ala Leu Ser Leu<br>              65                70                75 | 243 |
| ggt aaa gcc cca tgc aag gtg ttg gtc aac tat gcc agg tca tcc atg<br>Gly Lys Ala Pro Cys Lys Val Leu Val Asn Tyr Ala Arg Ser Ser Met<br>       80                  85                90 | 291 |
| caa gct gag gag gtt tcc aac ttg att gag gcg ttt ggt gga caa gct<br>Gln Ala Glu Glu Val Ser Asn Leu Ile Glu Ala Phe Gly Gly Gln Ala<br>   95                  100              105 | 339 |
| ctt acc ttc gag gga gat gtt tca aat gag gcc gat gtg gaa tct atg<br>Leu Thr Phe Glu Gly Asp Val Ser Asn Glu Ala Asp Val Glu Ser Met<br> 110                 115              120 | 387 |
| att aga act gca gtt gat gct tgg gga act gtt gat gta ttg gta aac<br>Ile Arg Thr Ala Val Asp Ala Trp Gly Thr Val Asp Val Leu Val Asn<br>125                 130               135              140 | 435 |
| aat gca gga att act cga gat ggt ttg tta atg aga atg aag aaa tca<br>Asn Ala Gly Ile Thr Arg Asp Gly Leu Leu Met Arg Met Lys Lys Ser<br>               145               150              155 | 483 |
| caa tgg cag gaa gtt att gat ctg aat ctc act ggt gtt ttt ctt tgc<br>Gln Trp Gln Glu Val Ile Asp Leu Asn Leu Thr Gly Val Phe Leu Cys<br>           160               165              170 | 531 |
| atg cag gca gca gca aag att atg acg atg aaa aag aag gga agg ata<br>Met Gln Ala Ala Ala Lys Ile Met Thr Met Lys Lys Lys Gly Arg Ile<br>       175                180              185 | 579 |
| atc aat att aca tca gtt att ggt cag gtt ggc aat gtt gga caa gcc<br>Ile Asn Ile Thr Ser Val Ile Gly Gln Val Gly Asn Val Gly Gln Ala<br>   190                 195              200 | 627 |

```
aat tat agt gct gca aag gca ggg gta att ggc ctc aca aaa agt gct      675
Asn Tyr Ser Ala Ala Lys Ala Gly Val Ile Gly Leu Thr Lys Ser Ala
205                 210                 215                 220 gcc agg gaa tat gct agc aga aac atc act gtt aat gca gta gcc cct      723
Ala Arg Glu Tyr Ala Ser Arg Asn Ile Thr Val Asn Ala Val Ala Pro
                225                 230                 235 ggg ttt att gca tct gat atg act gcc aat cta cga cca ggc att gag      771
Gly Phe Ile Ala Ser Asp Met Thr Ala Asn Leu Arg Pro Gly Ile Glu
            240                 245                 250 aaa aaa aga ttg gaa tta atc ccc tta gga aga ctt ggc caa cca gaa      819
Lys Lys Arg Leu Glu Leu Ile Pro Leu Gly Arg Leu Gly Gln Pro Glu
        255                 260                 265 gaa gtt gct gga ctt gtg gaa ttc ttg gct ctt aat cct gct gcc aat      867
Glu Val Ala Gly Leu Val Glu Phe Leu Ala Leu Asn Pro Ala Ala Asn
    270                 275                 280 tac atc act ggg cag gtg ttc acc att gat gga ggt ttg gca atg          912
Tyr Ile Thr Gly Gln Val Phe Thr Ile Asp Gly Gly Leu Ala Met
285                 290                 295 tgagtctcag gaatctgttt ccgtatatag caacttgaac ttctttactt cacagttcat    972
ctcaaaggcc acagaatttc aacttctgtc atggtgctag tttgttctat gctgatttat    1032
gctcaagcta gtaatacgtg gtgacttatt gtagaagttt agttgagctt tttaacaggt    1092
tgcttcttga gatgaattcg acatattgct gcattttggt gactcttatg ggtcacatta    1152
cattttacat ttcctgcaat ttaccaattt tgggccttat cttttcctaa tgatgagatg    1212
cttgcggtca tttcggaata aaaaaaaaaa aaaaaa                              1248

<210> SEQ ID NO 8
<211> LENGTH: 299
<212> TYPE: PRT
<213> ORGANISM: Glycine max

<400> SEQUENCE: 8

Met Gly Ser Leu Ala Arg Pro Asn Ser Leu Phe Phe Arg Thr Lys Gly
 1               5                  10                  15

Pro Gly Arg Ala Arg Lys Val Pro Ser Gln Val Leu Ala Phe Gln Arg
             20                  25                  30

Ser Asn Ser Asn Gly Ser Phe Pro Ser Glu Gln Leu Glu Leu Glu
         35                  40                  45

Ala Ser Gln Lys Asn Met Glu Ala Pro Val Val Val Thr Gly Ala
     50                  55                  60

Ser Arg Gly Ile Gly Arg Ala Ile Ala Leu Ser Leu Gly Lys Ala Pro
65                  70                  75                  80

Cys Lys Val Leu Val Asn Tyr Ala Arg Ser Ser Met Gln Ala Glu Glu
                 85                  90                  95

Val Ser Asn Leu Ile Glu Ala Phe Gly Gly Gln Ala Leu Thr Phe Glu
            100                 105                 110

Gly Asp Val Ser Asn Glu Ala Asp Val Glu Ser Met Ile Arg Thr Ala
        115                 120                 125

Val Asp Ala Trp Gly Thr Val Asp Val Leu Val Asn Asn Ala Gly Ile
    130                 135                 140

Thr Arg Asp Gly Leu Leu Met Arg Met Lys Lys Ser Gln Trp Gln Glu
145                 150                 155                 160

Val Ile Asp Leu Asn Leu Thr Gly Val Phe Leu Cys Met Gln Ala Ala
                165                 170                 175

Ala Lys Ile Met Thr Met Lys Lys Lys Gly Arg Ile Ile Asn Ile Thr
            180                 185                 190
```

```
Ser Val Ile Gly Gln Val Gly Asn Val Gly Gln Ala Asn Tyr Ser Ala
        195                 200                 205

Ala Lys Ala Gly Val Ile Gly Leu Thr Lys Ser Ala Ala Arg Glu Tyr
    210                 215                 220

Ala Ser Arg Asn Ile Thr Val Asn Ala Val Ala Pro Gly Phe Ile Ala
225                 230                 235                 240

Ser Asp Met Thr Ala Asn Leu Arg Pro Gly Ile Glu Lys Lys Arg Leu
                245                 250                 255

Glu Leu Ile Pro Leu Gly Arg Leu Gly Gln Pro Glu Glu Val Ala Gly
            260                 265                 270

Leu Val Glu Phe Leu Ala Leu Asn Pro Ala Ala Asn Tyr Ile Thr Gly
        275                 280                 285

Gln Val Phe Thr Ile Asp Gly Gly Leu Ala Met
        290                 295
```

<210> SEQ ID NO 9
<211> LENGTH: 1680
<212> TYPE: DNA
<213> ORGANISM: Pseudomonas fluorescens
<220> FEATURE:
<221> NAME/KEY: misc_feature
<222> LOCATION: (1)...(1680)
<223> OTHER INFORMATION: SEQ ID NO:1 from WO 01/23580

<400> SEQUENCE: 9

| | | | | |
|---|---|---|---|---|
| atgagcaaca | agaacaatga | agacctgcag | cgccaagcct | ctgagaatac | cctcgggctg | 60 |
| aacccggtga | tcggcatccg | cggcaaggat | ctgctgacct | ccgcgcgcat | ggtcatgctg | 120 |
| caggccatca | agcagccctt | ccacagtgcc | aagcacgtcg | cccatttcgg | ggtcgagctt | 180 |
| aaaaacgtcc | tgctcggctc | ttcggccctg | cagccggaag | ccgacgaccg | tcgcttcgcg | 240 |
| gacccggcct | ggagccagaa | ccccctctac | aagcgctacc | tgcagaccta | cctcgcctgg | 300 |
| cgcaaggaac | tgcaccagtg | gatcgagcac | agcgacctgt | cgtcgtccga | taccagccgc | 360 |
| ggccacttcg | tgatcaacct | gatgaccgaa | gccatggccc | caccaacac | catggccaac | 420 |
| ccggcggcgg | tgaagcgctt | cttcgaaacc | ggcggcaaga | gcctgctcga | cggcctctcg | 480 |
| cacctggcca | aggacctggt | caacaacggc | ggcatgccca | gccaggtcaa | catggacgcc | 540 |
| ttcgaggtcg | gcaagaacct | cgccaccacc | gaaggcgccg | tggtcttccg | caatgacgtg | 600 |
| ctggagctga | tccagtacaa | gcccatcacc | gagcaggtgc | acgagcgccc | gctgctggtg | 660 |
| gtgccgccgc | agatcaacaa | gttctacgtc | ttcgacctgt | cccaggagaa | gagcctggcg | 720 |
| cgcttcaacc | tgcgcaacgg | catccagacc | ttcatcgtca | gctggcgcaa | cccgaccaag | 780 |
| gcccagcgcg | aatggggcct | gtcgacctac | atcgaggcgc | tcaaggaaac | catcgaggtg | 840 |
| gtgctgaaga | tcaccggcgc | caaggacctc | aacatgctcg | gtgcctgctc | cggcggcatc | 900 |
| accacggtcg | ccctgctggg | ccactaccag | gcgatcggcg | agcacaaggt | gaacgccttc | 960 |
| acgcagttgg | tcagcgtgct | cgacttcaac | ctggacaccc | aggtcgcgct | gttcgccgac | 1020 |
| gaaaccaccc | tggaggccgc | caagcgccgc | tcctaccagt | ccggcgtgct | ggaaggcaag | 1080 |
| gaaatggcca | aggtcttcgc | ctggatgcgc | cccaacgacc | tgatctggaa | ctactgggtg | 1140 |
| aacaactacc | tgctcggcaa | cgagccgccg | gtgttcgaca | tcctctactg | gaacaacgac | 1200 |
| accacgcgcc | tgcccgccgc | cttccacggc | gagttggtgg | agatgttcaa | gaccaacccg | 1260 |
| ctgaccgcc | ccgacgggct | ggaggtctgc | ggcaccccaa | tcgacctaaa | gaaggtcacc | 1320 |
| tgcgacttct | tctgcgtggc | cggcaccacc | gaccacatca | cccccttggga | agcctgctac | 1380 |

-continued

```
cgctccgccc gcctgctggg cggcaaatgc gagttcgtgc tgtccaacag cgggcacatc    1440
cagagcatcc tcaaccccc gggcaaccc aaggcgcgct tctccaccaa cagcgagatg    1500
ccggcggacc cgaaggagtg gcaggaaaac gccaccaagc acgccgactc ctggtggctg    1560
tactggcaaa cctggctggc ggagcgctcg ggcaagacca agaaagccag cttcaccctc    1620
ggcaacaagg cctacccggc cggcgaggct tcgccaggga cctatgtcca cgaacgttga    1680
```

<210> SEQ ID NO 10
<211> LENGTH: 1683
<212> TYPE: DNA
<213> ORGANISM: Pseudomonas fluorescens
<220> FEATURE:
<221> NAME/KEY: misc_feature
<222> LOCATION: (1)...(1683)
<223> OTHER INFORMATION: SEQ ID NO:3 from WO 01/23580

<400> SEQUENCE: 10

```
atgcgagaga aacaggtgtc gggagccttg ccggtccccg ctaactacat gaacgcgcag     60
agcgccattg tcggcttgcg aggcaaggac ctggcctcca ccgtccgcac cctcgccctg    120
cagggcttga agcaccccgt gcacagcgcc cgccacgtcc tcgccttcgg cggccagctg    180
ggccgcgtat tgatgggcga caccccgcac aagcccaacc cgcaggacgc gcgcttcgcc    240
gatccctcct ggagccacaa cccgttctac cgtcgcggct gcaggccta cctggcctgg    300 cagaaacaac tctatgcctg ggtcgaggac agcgacctca ccgacgatga ccgcgcccgt    360
gcgcgcttcg tcctggccct ggtcagcgac gccatggcgc cctccaacag cctgctcaac    420
cccctcgcgg tgaaggagct gttcaacacc ggcggcctca gcctgctcaa tggcgcgcgc    480
cacctgctgg acgatgtgct gaacaacaac gccatgccgc ccaggtcag caagcactcc    540 ttcgagatcg gccgcaacct ggcaaccacg cccgggtcgg tggtctatcg caacgagctg    600
ctggaactga tccagtacaa gccgatgagc gagaagcagt acctcaagcc tctgctgatc    660
gtcccgccgc aaatcaacaa gttctacatc ttcgacctct cgccggagaa gagcttcgtc    720
cagtacgcgc tgaagaatgg cctgcaggtg ctcatggtca gctggcgcaa ccccgatgcg    780
cgccaccgcg aatggggcct gtccaccat gtgcaggcgc tggagcaggc ggtcgacgtg    840
gcccgcgcca tcaccggcag caaggacgtc aacctgatgg gcgcctgcgc cggcggcctg    900
accatcgccg ccctgcaggg ccacctccag gccaagcgcc aactacgcaa ggtcagcagc    960
gccagctacc tggtcagcct gctggacagc caggtcgaaa gccccgccgc cctgttcgcc    1020
gacgaacaga ccctggaggc ggccaagcgc cgctcctacc agcacggcgt cctggacggc    1080
cgcgacatgg cgaagatctt cgcctggatg cgccccaacg acctggtgtg gaactacttc    1140
gtcaacaact acctgctggg ccgtcagccg ccggccttcg acatcctcta ctggaacaac    1200
gacaacaccc gcctgcccgc cgccttccac ggcgacctgc tggacttctt caagcacaac    1260
ccgctgaccc ggggcggcgc gctggaaatc tgcggcaccc ccatcgacct gcagaaggtc    1320
acggtggaca gcttcagcgt ggccggtatc aacgaccaca tcaccccctg gacgcggtc    1380 tatcgctcgg cgcggctgct gggtggcgag agccgcttcg tgctgtccaa cagcgggcac    1440
atccagagca tcctcaaccc accgggcaac cccaaggcca actacctgga aaacggcaag    1500
ctcagctcgg accaccgcgc ctggtactac gacgcgaaga acgtgcaggg cagctggtgg    1560
```

```
ccggagtggc tgagctggat ccaggcgcgc tcggggggagc agcgcgaaac cctggtcacc    1620
ctcggcaacc aggcccaccc acccatggag gcggcacccg gcacctacgt gcacgtgcgc    1680
tga                                                                  1683
```

OAR POLYNUCLEOTIDES, POLYPEPTIDES AND THEIR USE IN PHA PRODUCTION IN PLANTS

CROSS-REFERENCE TO RELATED APPLICATION

This application is a divisional of U.S. Utility application Ser. No. 10/926,499, filed Aug. 26, 2004 now U.S. Pat. No. 7,129,395, which is a divisional of U.S. Utility application Ser. No. 10/024,806, filed Dec. 19, 2001, now U.S. Pat. No. 6,806,401, which claims the benefit of U.S. Provisional Application No. 60/258,417, filed Dec. 27, 2000, each of which is hereby incorporated herein in its entirety by reference.

FIELD OF THE INVENTION

The invention relates to compositions and methods for producing polyhydroxyalkanoates in transformed plants and transformed host cells.

BACKGROUND OF THE INVENTION

Polyhydroxyalkanoates (PHAs) are polyesters of hydroxyalkanoates which are naturally produced by a large variety of bacteria and fungi. PHAs are biodegradable and renewable, thereby providing an attractive alternative to petroleum-based plastics. However, high production cost has limited the widespread use of PHAs derived from bacterial fermentation. One alternative to reduce cost, production of PHAs in agricultural crops, has been regarded as promising. Small amounts of the PHA have been produced in the cytosol, plastids and peroxisomes of genetically engineered plants. See Poirier (1999) *Curr. Opin. Biotechnol.* 10(2):181-5; Madison et al. (1999) *Microbiol. Mol. Biol. Rev.* 63(1):21-53).

PHA synthases catalyze polymerization of hydroxyacyl-CoA substrates into PHA. The substrate specificity of this class of enzymes varies across the spectrum of PHA-producing organisms. The variation in substrate specificity of PHA synthases is supported by indirect evidence observed in heterologous expression studies (Lee et al. (1995) *Appl. Microbiol. Biotechnol.* 42:901 and Timm et al. (1990) *Appl. Microbiol. Biotech.* 33:296).

Until recently, the only PHA that has been produced in plants was polyhydroxybutyrate (PHB), a homopolymer of 3-hydroxybutyric acid (John et al. (1996) *Proc. Natl. Acad. Sci. USA* 93:12768-12773; Nawrath et al. (1994) *Proc. Natl. Acad. Sci. USA* 91:12760-12764; Padgette et al. (1997) *Plant Physiol.* 114 (Suppl.) 3S; Poirier et al. (1992) *Science* 256:520-523)). Because this polymer is crystalline and brittle with a melting point too close to its degradation point, PHB is difficult to mold into desirable products (Lee (1996) *Biotechnol. Bioeng* 491.1-14).

Many bacteria make copolymers of 3-hydroxyalkanoic acids with a carbon chain length greater than or equal to five (Steinbuchel (1991) *Biomaterials: Novel Materials from Biological Materials*, ed. Byrom (New York: Macmillan Publishers Ltd.), pp. 123-213). Such copolymers are polyesters composed of different 3-hydroxyalkanoic acid monomers. Depending on the composition, these copolymers can have properties ranging from firm to elastic (Anderson et al. (1990) *Microbiol. Rev.* 54:450-472; Lee, (1996) *Biotechnol. Bioeng.* 49:1-14). Unlike the homopolymeric PHB, the PHA copolymers are suitable for a variety of applications because these copolymers exhibit a wide range of physical properties.

Initial attempts at producing PHA in plants involved producing PHA in the cytosol, but production of PHA in this cellular compartment proved toxic to the plant (Poirier et al. (1992) *Science* 256:520-523). This problem was overcome by targeting the PHA-producing enzymes to plastids (Nawrath et al. (1994) *Proc. Natl. Acad Sci. USA* 91:12760-12764). In either cellular compartment, however, only PHB was accumulated, not any of the copolymers. With both of these methods, the genes from Ralstonia eutropha were used. The PHA synthase of this bacterium can utilize only short chain ($C_3$-$C_5$) monomers (Steinbuchel (1991) *Biomaterials: Novel Materials from Biological Materials*, ed. Byrom (New York: Macmillan Publishers Ltd.), pp. 123-213). Later, copolymer production in *Arabidopsis* and canola was reported by Slater et al. (1999) *Nature Biotechnology* 17: 1011-1016.

The synthesis of PHA containing 3-hydroxyalkanoic acid monomers ranging from six to sixteen carbons in *Arabidopsis thaliana* was reported (Mittendorf et al. (1998) *Proc. Natl. Acad. Sci. USA* 95:13397-13402). To accumulate PHA, the *Arabidopsis* plants were transformed with a nucleotide sequence encoding PHA synthase from *Pseudomonas aeruginosa* that was modified for peroxisome targeting by the addition of a nucleotide sequence encoding the C-terminal 34 amino acids of a *Brassica napus* isocitrate lyase. In these plants, PHA was produced in glyoxysomes, leaf-type peroxisomes, and vacuoles. However, PHA production was very low in the *Arabidopsis* plants, suggesting that either the introduced PHA synthase did not function properly in the intended organelle, or more likely that the necessary substrates for the introduced PHA synthase were present at levels that were limiting for PHA synthesis. While this report demonstrated that PHA can be produced in peroxisomes of plants, the level of PHA produced in the plants was far below levels necessary for the commercial production of PHA in plants. Thus, methods and compositions directed to increasing the level of substrate for PHA synthases are needed for production of PHA in plants.

There are two types of fatty acid synthase (FAS). In type I FAS, various enzyme activities are located on different domains of a multifunctional protein. In type II FAS, these enzyme activities are catalyzed by individual polypeptides. 3-oxoacyl-[acyl carrier protein(ACP)] reductase (OAR) is a component of the type II FAS. This enzyme reversibly reduces β-ketoacyl-ACP, the condensation product of an acetyl residue and a nascent acyl-ACP, to β-hydroxyacyl-ACP. In vitro, OAR also uses 3-ketoacyl-CoA as a substrate to catalyze formation of 3-hydroxyacyl-CoA. This use of 3-ketoacyl-CoA is at a lower efficiency than the use of β-ketoacyl-ACP as substrate (Shimakata et al. (1982) *Arch. Biochem. Biophys.* 218(1): 77-91).

NADPH-dependent OAR from *Spinacia oleracea* has been described to catalyze the forward reaction of reducing β-ketoacyl-ACP, more than seventeen times faster than the reverse dehydrogenation reaction, at neutral or acidic pH. This OAR has also been shown to use only D-3-hydroxybutyryl-ACP as a substrate but not the L-form counterpart.

NADH-dependent forms of OARs have been described from plant species such as castor bean and avocado (Shimakata et al. (1982) *Arch. Biochem. Biophys.* 218(1): 77-91; Caughey et al. (1982) *Eur. J Biochem.* 123(3): 553-61). Taguchi et al. have shown that over-expression of a bacterial NADPH-dependent OAR increases D-3-hydroxyacyl-CoA monomer supply for PHA synthase and leads to accumulation of PHAs in *E. coli* (Taguchi et al. (1999) *Fems. Microbiol. Lett.* 176(1): 183-190).

Thus, methods and compositions directed to plant OARs are needed for increasing the level of substrate for PHA synthases, and for production of PHA in plants.

SUMMARY OF THE INVENTION

Compositions and methods directed to producing PHA in host cells and plants are provided, including PHA copolymers. The compositions are directed to isolated nucleic acid molecules encoding 3-oxoacyl-[acyl carrier protein(ACP)] reductase (OAR) polypeptides. Expression cassettes comprising the nucleotide sequences encoding the OAR enzymes are also provided.

For PHA production in host cells, such as bacteria, with one or more endogenous PHA synthases, the methods involve genetically manipulating the host cell to produce one or more OAR enzymes. The methods comprise stably integrating in the genome of a host cell nucleotide sequences encoding OAR enzymes.

For PHA production in plants, the methods involve genetically manipulating a plant to produce one or more OAR enzymes. If desired, the plants can also be transformed with nucleotide sequences encoding additional enzymes that are necessary for, or favorably affect, the synthesis of PHA in the plants. Such enzymes include, for example, one or more PHA synthases. The OAR enzymes, and any other desired enzymes, can be targeted in the plant to the peroxisomes by operably linking a peroxisome-targeting sequence to a sequence encoding the enzyme. The methods comprise stably integrating in the genome of a plant nucleotide constructs comprising nucleotide sequences encoding OAR enzymes, PHA synthases, and/or any other desired enzymes for PHA synthesis in a plant or part thereof.

Also provided are plants, plant tissues, plant cells, and seeds thereof, that are genetically manipulated to produce one or more OAR enzymes. Further provided are plants, plant tissues, plant cells, and seeds thereof comprising stably integrated in their genomes a nucleotide sequence encoding an OAR and a nucleotide sequence encoding a PHA synthase. Such plants, plant tissues, plant cells, and seeds can additionally comprise stably integrated in their genomes one or more additional nucleotide sequences which encode enzymes that favorably affect PHA synthesis.

DETAILED DESCRIPTION OF THE INVENTION

Compositions and methods for the production of biodegradable polyesters in plants and other organisms are provided. In particular, nucleotide sequences for 3-oxoacyl-[acyl carrier protein (ACP)] reductase (OAR) genes are provided. More particularly, oar1 and oar2 genes from maize, and oar1 and oar2 genes from soybean are provided (SEQ ID NOs: 1, 3, 5, and 7). The sequences can be used in combination with other sequences, including but not limited to PHA and PHB synthases, to produce polyhydroxyalkanoates. These sequences can be provided with peroxisome-targeting sequences for targeting to the peroxisomes. Also provided are polypeptides encoded by such nucleotide sequences (SEQ ID NOs: 2, 4, 6, and 8).

The present invention provides for isolated nucleic acid molecules comprising nucleotide sequences encoding the amino acid sequences shown in SEQ ID NOs: 2, 4, 6, and 8. The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. An "isolated" nucleic acid (including protein encoding sequences) can be free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an OAR nucleotide sequence that encodes a biologically active portion of an OAR protein of the invention will encode at least 15, 25, 30, 50, 100, 150, 200, 250, 300, 350, 400, 450, 500, or 550 contiguous amino acids, or up to the total number of amino acids present in a full-length OAR protein of the invention (for example, 318, 312, 320, and 299 amino acid for SEQ ID NOs: 2, 4, 6, and 8 respectively). Fragments of an OAR enzyme nucleotide sequence that are useful as hybridization probes or PCR primers generally need not encode a biologically active portion of an OAR enzyme.

Thus, a fragment of an OAR enzyme nucleotide sequence may encode a biologically active portion of an OAR enzyme, or it may be a fragment that can be used as a hybridization probe or PCR primer using methods disclosed below. A biologically active portion of an OAR enzyme can be prepared by isolating a portion of one of the OAR enzyme nucleotide sequences of the invention, expressing the encoded portion of the an OAR enzyme (e.g., by recombinant expression in vitro), and assessing the activity of the encoded portion of the a OAR enzyme. Nucleic acid molecules that are fragments of an OAR enzyme nucleotide sequence comprise at least 16, 20, 50, 75, 100, 150, 200, 250, 300 350, 400, 450, 500, 550, 600, 650, 700, 800, 900, 1,000, 1,100, 1,200, or up to the number of nucleotides present in a full-length OAR nucleotide sequence disclosed herein (for example, 1326, 1286, 1398, and 1248 nucleotides for SEQ ID NOs: 1, 3, 5, and 7, respectively).

By "variants" is intended substantially similar sequences. For nucleotide sequences, conservative variants include those sequences that, because of the degeneracy of the genetic code, encode the amino acid sequence of one of the OAR polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an OAR protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein. Such variants may result from, for example, genetic polymorphism or from human manipulation. Biologically active variant proteins which are encompassed by the invention, and which are variants of a native OAR protein of the invention will have greater than 60%, about 70%, generally at least about 75%, 80%, 85%, preferably at least about 90%, 91%, 92%, 93%, 94%, 95%, 96%, 97%, and more preferably at least about 98%, 99%, or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of OAR proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. In this aspect of the present invention, conservative substitutions, such as exchanging one amino acid with another having similar properties, may be used.

Thus, the genes and nucleotide sequences of the invention include both the naturally occurring sequences as well as mutant forms. Likewise, the proteins of the invention encompass both naturally occurring proteins as well as variations and modified forms thereof. Generally, such variants will continue to possess the desired activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by OAR activity assays. See, for example, Shimakata et al. (1982) *Arch. Biochem. Biophys.* 218(1): 77-91; herein incorporated by reference. Variant nucleotide sequences and proteins also encompass sequences and proteins derived from a mutagenic and recombinogenic procedure such as DNA shuffling. With such a procedure, one or more different OAR coding sequences can be manipulated to create a new OAR enzyme possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the OAR gene of the invention and other known OAR genes to obtain a new gene coding for a protein with an improved property of interest, such as an increased Km or co-substrate specificity in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other bacteria. In this manner, methods such as PCR, hybridization, and the like can be used to identify such sequences based on their sequence homology to the sequences set forth herein. Sequences isolated based on their sequence identity to the entire OAR sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the OAR sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire OAR sequence disclosed herein, or one or more portions thereof, may be used as a probe capable of specifically hybridizing to corresponding OAR sequences and messenger RNAs. To achieve specific hybridization under a variety of conditions, such probes include sequences that are unique among OAR sequences and are preferably at least about 10 nucleotides in length, and most preferably at least about 20 nucleotides in length. Such probes may be used to amplify corresponding OAR sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m = 81.5°$ C. $+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with $\geq 90\%$ identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an OAR protein and which hybridize under stringent conditions to the OAR sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invention encompasses nucleotide constructs comprising the nucleic acids of the invention, and fragments and variants thereof; and methods utilizing these constructs. The nucleotide constructs of the present invention are not limited to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Methods are provided for producing PHA in host cells. Such host cells find use in the production of biodegradable thermoplastics. The methods involve transforming a host cell with a nucleic acid molecule encoding an OAR enzyme, including but not limited to the nucleic acid molecules of the invention encoding an OAR enzyme. Examples of known OAR encoding nucleic acids that can be used in the methods of the invention include those OAR encoding sequences described in Genbank accession number AF042860, EMBL accession number X75781, EMBL accession number X64566, and Genbank accession number T1 5143. While the invention is not limited to any particular mechanism, it is envisioned that active expression of one or more OAR encoding sequences leads to reduction of 3-ketoacyl-CoAs by the expressed OAR proteins, to form 3-hydroxyacyl-CoAs. In turn, 3-hydroxyacyl-CoAs are used as substrate by one or more PHA synthases, for PHA synthesis. 3-ketoacyl-CoAs are naturally produced in plants as intermediates in the β-oxidation cycle.

The methods additionally comprise growing the host cells for a sufficient length of time in conditions favorable for the production of PHA. The methods further involve extracting the PHA from the host cells or from the vicinity of the host cells, such as for example, a culture broth or solid medium. Host cells include non-human host cells including but not limited to plant cells, bacterial cells, yeast cells, fungal cells, algal cells and animal cells such as, for example, insect cells and nematode cells. The host cells of the invention may be single cells, colonies or clumps of cells, or cells within a multicellular structure or organism.

Methods for producing PHB in the cytosol or plastids of plants and for producing PHA in plant peroxisomes are known in the art. However, such methods do not achieve the synthesis of high levels of PHA in plants. The nucleotide sequences of the present invention find use in improved methods for transforming plant host cells and producing PHA in plants, particularly in the cellular compartments therein such as the cytosol, plastids and peroxisomes, more particularly in the peroxisomes.

Depending on the particular host cell, in addition to transforming with one or more OAR-encoding nucleic acid molecules, the methods further involve transforming the host cell with at least one additional nucleic acid molecule encoding a PHA synthase. In vitro, OAR prefers 3-ketoacyl-ACP to 3-ketoacyl-CoA as a substrate. However, while the invention is not limited by any particular mechanism, it is envisioned that in the methods of the present invention, the additional PHA synthase activity converts D-3-hydroxyacyl-CoA formed by OAR catalysis into PHAs, thus driving the OAR utilization of 3-ketoacyl-CoA substrate to proceed at a much higher rate in vivo.

In one embodiment, the PHA synthase utilized in the methods of the invention catalyzes the synthesis of PHA copolymers. By "PHA copolymer" is intended a polymer composed of at least two different 3-hydroxyalkanoic acid monomers. In another embodiment, such a PHA synthase catalyzes the synthesis of PHA copolymers comprised of 3-hydroxybutyric acid momomers and at least one additional monomer having a chain length of greater than four carbons. In yet another embodiment, such a PHA synthase catalyzes the synthesis of copolymers comprised of 3-hydroxybutyric acid monomers and at least one additional monomer having a hydroxyacyl-chain length of from about 5 to about 18 carbons. In further embodiments of the invention, the majority of PHA copolymers produced are comprised of monomers of chain-length $C_4$ to $C_{18}$.

PHA synthases utilized in the methods of the invention include those encoded by nucleotide sequences isolatable from *Pseudomonas oleovorans* (GenBank Accession No. M58445), *Pseudomonas putida* (Accession No. GenBank AF042276), *Pseudomonas aeruginosa* (EMBL Accession No. X66592), *Aeromonas caviae* (DDBJ Accession No. D88825) and *Thiocapsa pfennigii* (EMBL Accession No. A49465). Such PHA synthases additionally include the PHA synthases encoded by nucleotide sequences isolated from *Pseudomonas fluorescens* disclosed in WO 01/23580.

PHA synthases utilized in the methods of the invention are specific to the R— (or D—) forms of their substrate 3-hydroxyacyl-CoAs. Consistent with this specificity, the OAR enzymes of the present invention catalyze the formation of R— (or D-)3-hydroxyacyl-CoAs. For the purposes of the present invention, R-3-hydroxyacyl-CoAs and D-3-hydroxyacyl-CoAs are used interchangeably.

Methods for producing PHA in plants are provided. The methods involve genetically manipulating the genome of a plant to produce PHA. The invention encompasses plants and seeds thereof, that have been genetically manipulated to produce enzymes leading to PHA synthesis and expression cassettes containing coding sequences for such enzymes. The invention further encompasses genetically manipulated plant cells and plant tissues. More particularly, the invention encompasses plants, and seeds thereof, that have been genetically manipulated to produce OAR enzymes that produce substrates for PHA synthases, as well as those plants additionally manipulated to produce PHA synthases for utilizing these substrates.

The methods provided for producing PHA involve genetically manipulating the plant to produce at least one OAR enzyme to catalyze formation of substrate for PHA synthases. The plants of the invention each comprise in their genomes at least one stably incorporated nucleotide construct, each nucleotide construct comprising a coding sequence for an OAR enzyme operably linked to a promoter that drives the expression of a gene in a plant. Plants of the invention are genetically manipulated to produce an OAR enzyme of the invention. In one embodiment, the plants of the invention are additionally genetically manipulated to produce one or more PHA synthases, including, but not limited to, the PHA synthases described above. Such PHA synthases include those that are known to catalyze the synthesis of PHA copolymers. Such PHA synthases include, but are not limited to, those described in WO 01/23596; and those disclosed in WO 01/23580 (provided as SEQ ID NOs:9 and 10 in the sequence listing for the present application).

Additionally, a plant of the invention may comprise in its genome a nucleotide construct comprising a coding sequence for a PHA synthase capable of synthesizing PHB including, but not limited to, those encoded by nucleotide sequences isolatablefrom *Ralstonia eutropha* (GenBank Accession No. J05003), *Acinetobacter* sp. (GenBank Accession No. U04848), *Ralstonia latus* (GenBank Accession No. AF078795), *Azorhizobium caulinodans* (EMBL Accession No. AJ006237), *Comamonas acidovorans* (DDBJ Accession No. AB009237), *Methylobacterium extorquens* (GenBank Accession No. L07893), *Paracoccus denitrificans* (DDBJ Accession No. D43764) and *Zoogloea ramigera* (GenBank U66242). Thus, the invention encompasses plants, and seeds thereof, that have been genetically manipulated to produce enzymes that produce substrates for PHB synthases; as well as those additionally manipulated to produce PHB synthases for utilizing the substrates.

Any method for producing more than one enzyme in a plant may be utilized. In one embodiment, a plant is transformed with more than one construct in a transformation method. In another embodiment, a plant is transformed with one or more constructs comprising coding sequences for more than one enzyme described herein. In yet another embodiment, a transformed plant is re-transformed with one or more constructs. In a further embodiment, transformed plants are crossed with one another, to produce a plant producing more than one enzyme.

The nucleotide constructs of the invention each comprise a coding sequence for an OAR enzyme operably linked to a promoter that drives expression in a plant cell. Preferably, the promoters are selected from seed-preferred promoters, chemical-regulatable promoters, germination-preferred promoters and leaf-preferred promoters. In an embodiment of the present invention, each of the nucleotide constructs additionally comprises an operably linked nucleotide sequence encoding a peroxisome-targeting signal. The peroxisome-targeting signal may be native or endogenous to the particular OAR sequence, or it may be a heterologous peroxisome-targeting signal. It is recognized that, where plants are genetically manipulated to produce one or more OAR enzymes and one or more PHA synthases and where expression of the OAR coding sequences in the peroxisome is desired, each nucleotide construct comprising the OAR or PHA synthase coding sequence also comprises an operably linked peroxisome-targeting signal.

OAR enzymes of the invention include those that prefer NADH to NADPH as co-substrate since NADH is the predominant electron donor in the peroxisome. OAR enzymes of the invention also include those having kinetic properties that strongly favor the forward reaction, reduction of 3-ketoacyl-CoAs, and disfavor the reverse reaction, the dehydrogenation of D-3-hydroxyacyl-CoAs. The OAR enzymes of the invention further include, but are not limited to, those that are active in peroxisomal matrices. Additionally, the OAR enzymes or polypeptides of the invention include, but are not limited to, those that catalyze the formation of 3-hydroxyacyl-ACP, 3-hydroxyacyl-CoA, or both 3-hydroxyacyl-ACP and 3-hydroxyacyl-CoA.

The OAR enzyme sequences of the invention can possess one or more of the properties described above, including the ability to be targeted to peroxisomes, the ability to utilize NADH as co-substrate, the preference for the forward reaction of reduction of 3-ketoacyl-CoAs, and the ability to be active in the acidic environment of peroxisomes. Alternatively, these characteristics can be introduced into an OAR sequence of the invention by methods known in the art and otherwise described herein, such as site directed mutagenesis and DNA shuffling. For example, the NADH- or NADPH-binding domain of many proteins have been well characterized and a change of as few as three amino acids has been shown to alter the binding specificity from NADPH to NADH (Nishiyama et al. (1993) *J. Biol. Chem.* 268(7): 465MO). Furthermore, NADH-preferring forms of OARs have been described from plant species such as castor bean and avocado (Shimakata et al. (1982) *Arch. Biochem. Biophys.* 218(1): 77-91; Caughey et al. (1982) *Eur. J Biochem.* 123(3): 553-61), and can be used in DNA shuffling methods to confer NADH-preference to the OAR enzymes of the invention.

Alternatively, for utilizing NADPH-preferring OAR enzymes, it may be necessary to increase the level of NADPH in the peroxisome. Thus, the methods of the invention may additionally involve stably integrating into the genome of a plant a nucleotide construct comprising a nucleotide sequence encoding an NADH kinase or an NAD kinase and an operably linked promoter that drives expression in a plant cell. Such NADH and NAD kinases catalyze the synthesis of NADPH and NADP$^+$, respectively. Nucleotide sequences encoding such kinases include, but are not limited to DDJB Accession No. E131102 and EMBL Accession Nos. Z73544 and X84260. This construct may additionally comprise an operably linked peroxisome-targeting signal sequence. By targeting such NADH and NAD kinases to the peroxisome, the level of NADPH and NADP$^+$ can be increased in the plant peroxisome for use by enzymes, such as, for example, an NADPH-dependent 3-ketoacyl-CoA reductase.

Because PHA is not known to occur naturally in a plant, the biosynthetic pathway for PHA in plant additionally encompasses enzymes and products thereof that are involved in PHA synthesis which result from the genetic manipulation of the plant. By "intermediate molecule" is intended a precursor in the biosynthetic pathway for PHA in a plant. Intermediate molecules of the present invention include, but are not limited to, fatty acids and β-oxidation products derived therefrom, acetyl-CoA, acetoacetyl-CoA and other 3-ketoacyl-CoAs, 3-hydroxybutyryl-CoA and other 3-hydroxyacyl-CoAs.

Thus, it is recognized that for producing high levels of PHA copolymers in certain plants, particularly in their peroxisomes, it may be necessary to genetically manipulate plants to produce other enzymes involved in PHA synthesis; in addition to the OAR enzymes of the invention. Generally, these other enzymes are directed to the peroxisome to increase the synthesis of at least one intermediate molecule leading to increased levels of 3-ketoacyl-CoA For example, such an intermediate molecule may be a precursor for 3-ketoacyl-CoA synthesis; including but not limited to 3-hydroxyacyl-CoA, enoyl-CoA, and acyl-CoA; the formations of which are catalyzed by enoyl-CoA hydratase, acyl-CoA oxidase, and acyl-CoA synthetase, respectively. Thus, it is recognized that depending on the particular plant, endogenous levels of the OAR substrate, 3-ketoacyl-CoA, may be limiting the level of D-3-hydroxyacyl-CoA that can be produced by the expressed OAR. Alternatively, or additionally, it is recognized that levels of 3-ketoacyl-CoA for utilization by the expressed OAR can be increased by using antisense constructions to decrease or eliminate downstream utilization of 3-ketoacyl-CoA by enzymes other than OAR. For example, antisense constructs to the enzyme thiolase can be used to increase the levels of 3-ketoacyl-CoA to be utilized by the expressed OAR. It is recognized that, where increased production of D-(-)-3-hydroxybutyryl-CoA is desired, decrease or elimination of ketothiolase would not be desired.

Antisense constructions complementary to at least a portion of the messenger RNA (mRNA) for a corresponding sequence encoding an enzyme can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally sequences of at least 50 nucleotides, 100 nucleotides, 200 nucleotides, or greater may be used.

It is further recognized that levels of 3-ketoacyl-CoA for utilization by the expressed OAR can be increased by using constructions in the sense orientation to decrease or eliminate downstream utilization of 3-ketoacyl-CoA by enzymes other than OAR. That is, nucleotide sequences encoding endogenous enzymes catalyzing downstream utilization of 3-ketoacyl-CoA may be used in the sense orientation to suppress the expression of corresponding endogenous genes in plants. For example, sense constructs to the enzyme thiolase can be used to increase the levels of 3-ketoacyl-CoA to be utilized by the expressed OAR. Methods for suppressing gene expression in plants using nucleotide sequences in the sense orientation are known in the art. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The methods of the invention comprise genetically modifying plants to produce; in addition to the OAR and PHA synthase described above, one, two, three, four, five or more additional enzymes involved in PHA synthesis. Examples of such enzymes include but are not limited to enoyl-CoA hydratase, acyl-CoA oxidase, and acyl-CoA synthetase, Alternatively, or additionally, the methods of the invention comprise genetically modifying plants to produce; in addition to the OAR and PHA synthase described above, one, two, three, four, five or more antisense constructs corresponding to enzymes involved in PHA synthesis. In one method of the invention, each nucleotide construct comprising the coding sequence of one of these additional enzymes is operably linked to a promoter that drives expression in a plant and also to a nucleotide sequence encoding a peroxisome-targeting signal sequence. Depending on the plant, the addition of one or more of these enzymes, and/or antisense constructs, may be necessary to achieve high-level PHA synthesis in the plant.

The methods of the invention additionally comprise growing the plant under conditions favorable for PHA production, harvesting the plant, or one or more parts thereof, and isolating the PHA from the plant or part thereof. Such parts include, but are not limited to, seeds, leaves, stems, roots, fruits and tubers. The PHA may be isolated or extracted from the plant or part thereof by methods known in the art. See, U.S. Pat. Nos. 5,942,597, 5,918,747, 5,899,339, 5,849,854 and 5,821,299; herein incorporated by reference. See also, EP 859858A1, WO 97/07229, WO 97/07230 and WO 97/15681; herein incorporated by reference.

The nucleotide sequences of the invention can be used in methods for producing PHA in plants. Such methods can be used in conjunction with methods known in the art for producing PHA in plants, particularly in peroxisomes. The methods of the invention encompass utilizing the nucleotide sequences of the invention to increase the synthesis of an intermediate molecule in PHA synthesis. Such an intermediate molecule can be limiting for PHA synthesis in the peroxisome and increasing the synthesis of such a molecule in the peroxisome increases the level of PHA produced in a plant. Intermediate molecules that can be limiting for PHA synthesis include, for example, R-(−)-3-hydroxybutyryl-CoA, other R-(−)-3-hydroxyacyl-CoAs, acetoacetyl-CoA and other 3-ketoacyl-CoAs. It is recognized that increasing the synthesis of an intermediate molecule in a plant peroxisome may not lead to an increased level of the intermediate molecule in the plant because the intermediate molecule may be further metabolized into, for example, PHA.

The nucleotide sequences of the invention can be used in conjunction with other methods for producing PHA in plants including, but not limited to, methods that involve utilizing 3-ketoacyl-CoA reductase to form 3-hydroxyacyl-CoA substrate for PHA synthases, and/or methods that involve increasing the levels of R-(−)-3-hydroxybutyryl-CoA, other R-(−)-3-hydroxyacyl-CoAs, acetoacetyl-CoA and other 3-ketoacyl-CoAs. Examples of such methods are described in WO 01/23596 and WO 01/23580; both of which are hereby incorporated herein in their entirety by reference.

In this aspect, the invention provides methods for producing increased levels of PHA in the peroxisomes of plants that involve increasing the synthesis of one or more intermediate molecules in the peroxisome, including, and in addition to, increasing the level of R-(−)-3-hydroxyacyl-CoAs by transformation with OAR-encoding sequences. In one aspect of the invention, plants are genetically manipulated to increase the synthesis of R-(−)-3-hydroxyacyl-CoAs. In a second aspect of the invention, plants are genetically manipulated to increase the synthesis of a specific R-(−)-3-hydroxyacyl-CoA, R-(−)-3-hydroxybutyryl-CoA. In a third aspect of the invention, the first and second aspects are combined to provide plants that are genetically manipulated to increase the synthesis of both R-(−)-3-hydroxyacyl-CoAs and R-(−)-3-hydroxybutyryl-CoA.

Further, it is recognized that each of the aspects of the invention may be used to produce PHA with substantially different monomer compositions. In particular, the level of 3-hydroxybutyric acid in the PHA produced in a plant will vary with each aspect. For each particular type of plant, PHA produced by plants of the second or third aspect of the invention is expected to have a higher 3-hydroxybutyric acid monomer content than PHA produced by plants of the first aspect. Similarly, PHA produced by plants of the second aspect is expected to have a higher 3-hydroxybutyric acid monomer content than PHA produced by plants of the third aspect.

In a first embodiment of the invention, methods are provided for producing PHA involving genetically manipulating a plant for increased synthesis of R-(−)-3-hydroxyacyl-CoA, a key intermediate molecule in PHA synthesis in the peroxisome. The methods comprise stably integrating into the genome of a plant one or more nucleotide constructs comprising a coding sequence for an enzyme that catalyzes the formation of R-(−)-3-hydroxyacyl-CoA substrate of PHA synthase, wherein at least one such construct comprises at least one OAR nucleotide sequence described herein. Additionally, the plant can also comprise one or more nucleotide constructs comprising a coding sequence for a PHA synthase. In β-oxidation in plant peroxisomes, acyl-CoA oxidase catalyzes the conversion of fatty acyl-CoA into 2-enoyl-CoA which is subsequently converted to S-(+)-3-hydroxyacyl-CoA via the 2-enoyl-CoA hydratase of a multifunctional protein. While some R-(−)-3-hydroxyacyl-CoA may be present in peroxisomes, the level is believed to be very low and insufficient to allow for the synthesis of an economically acceptable level of PHA in a plant. Furthermore, all known PHA synthases require that 3-hydroxyacyl-CoA monomers to be in R-(−)-form for PHA synthesis. To overcome the substrate limitation for PHA synthesis, the present invention discloses methods for PHA synthesis which involve providing a plant with an OAR enzyme in its peroxisomes that catalyzes the formation of R(−)-3-hydroxyacyl-CoA. By genetically manipulating a plant to increase the synthesis of R-(−)-3-hydroxyacyl-CoA, the present invention overcomes a major impediment to achieving high-level production of PHA copolymers in plants.

In addition to an OAR enzyme described herein, the present invention encompasses utilizing an enoyl-CoA hydratase that catalyzes the synthesis of R-(−)-3-hydroxyacyl-CoA, particularly a 2-enoyl-CoA hydratase from *Aeromonas caviae*. Alternatively, two proteins from yeast may each be utilized as the additional enzyme. One such protein is the yeast multifunctional protein (GenBank Accession No. M86456) which possesses a 2-enoyl-CoA hydratase activity and a 3-hydroxyacyl-CoA dehydrogenase activity. The hydratase activity of the multifunctional protein is known to yield R-(−)-3-hydroxyacyl-CoA products. If necessary, the dehydrogenase activity may be neutralized by methods known to those of ordinary skill in the art such as, for example, site-directed mutagenesis, and truncation of the coding sequence to only the portion necessary to encode the desired hydratase activity. The other yeast protein is an enzyme identified as a 3-hydroxybutyryl-CoA dehydrogenase (Leaf et al. (1996) *Microbiology* 142:1169-1180). The gene encoding this enzyme may be cloned from *Saccharomyces cerevisiae*, sequenced and employed in the methods of the present invention. It is recognized that the nucleotide sequence encoding this enzyme may need to be modified to alter the amino acid sequence of the enzyme in such a manner as to favorably affect the production of R-(−)-3-hydroxyacyl-CoA in a plant. Such modifications may affect characteristics of the enzyme such as, for example, substrate specificity, product specificity, product inhibition substrate binding affinity, product binding affinity, and the like. A method such as, for example, DNA shuffling may be employed to modify this enzyme in the desired manner. Any method known in the art for altering the characteristics of an enzyme to favorably affect the mass action ratio toward the desired product is encompassed by the methods of the present invention. Such methods typically involve modifying at least a portion of the nucleotide sequence encoding the enzyme and include, but are not limited to, DNA shuffling, site-directed mutagenesis, and random mutagenesis.

In a second embodiment of the invention, methods for producing PHA are provided which involve genetically manipulating a plant for increased synthesis of R-(−)-3-hydroxybutyryl-CoA, a substrate of PHA synthase, in peroxisomes. The methods of the invention provide a plant that is genetically manipulated for increased synthesis of a substrate for a PHA synthase and thus provide a plant that is genetically manipulated for high-level PHA synthesis in its peroxisomes. The methods involve stably integrating into the genome of a plant one or more primary nucleotide constructs comprising a coding sequence for a 3-ketoacyl-CoA reductase, wherein at least one such construct comprises a nucleotide sequence encoding an OAR enzyme of the invention. In another embodiment the methods further involve stably integrating into the genome of a plant one or more secondary nucleotide constructs comprising a coding sequence for a PHA synthase. In another embodiment, the methods further involve stably integrating into the genome of a plant one or more tertiary nucleotide constructs comprising a coding sequence for an acetyl-CoA:acetyl transferase. The primary, secondary, and tertiary constructs each additionally comprise an operably linked promoter that drives expression in a plant cell, and if necessary, an operably linked peroxisome-targeting signal sequence. Acetyl-CoA:acetyl transferase, also referred to as ketothiolase, catalyzes the synthesis of acetoacetyl-CoA from two molecules of acetyl-CoA. Acetoacetyl-CoA may then be converted into R-(−)-3-hydroxybutyryl-CoA via a reaction catalyzed by an enzyme having 3-ketoacyl-CoA reductase activity, such as an OAR enzyme of the invention. The PHA synthase utilized in this embodiment of the invention includes a PHB synthase and/or any PHA synthase capable of accepting $C_4$ substrate, including PHA synthases that accept $C_4$— and longer substrates.

3-ketoacyl-CoA reductases utilized in the methods of the invention are those that utilize NADH and include, but are not limited to, at least a portion of the multifunctional proteins from yeast (GenBank Accession No. M86456), and rat (GenBank Accession No. U37486), wherein such a portion comprises a 3-ketoacyl-CoA reductase domain.

In the methods of the invention, however, NADPH-dependent 3-ketoacyl-CoA reductases can also be employed including, but not limited to, the 3-ketoacyl-CoA reductases encoded by GenBank Accession No. J04987 and EMBL Accession No. Z80156. Acetyl-CoA:acetyl transferases that can be utilized in the methods of the invention include, but are not limited to a radish acetyl-CoA:acetyl transferase encoded by the nucleotide sequence having EMBL Accession No. X78116.

If necessary to increase the level of NADPH in the peroxisome, the methods of this embodiment may additionally involve, stably integrating into the genome of a plant, a quaternary nucleotide construct comprising a nucleotide sequence encoding a NADH kinase or an NAD kinase and an operably linked promoter that drives expression in a plant cell. Such NADH and NAD kinases catalyze the synthesis of NADPH and $NADP^+$, respectively. Nucleotide sequences encoding such kinases include, but are not limited to, DDJB Accession No. E131102 and EMBL Accession Nos. Z73544 and X84260. The fourth construct may additionally comprise an operably linked peroxisome-targeting signal sequence. By targeting such NADH and NAD kinases to the peroxisome, the level of NADPH and $NADP^+$ can be increased in the plant peroxisome for use by enzymes, such as, for example, an NADPH-dependent 3-ketoacyl-CoA reductase.

In a third embodiment of the invention, methods are provided for producing PHA in a plant involving genetically manipulating a plant for increased synthesis of R-(−)-3-hydroxybutyryl-CoA and other R-(−)-3-hydroxyacyl-CoA molecules. Such methods provide a plant that is genetically manipulated to overcome substrate limitations for PHA copolymer synthesis in its peroxisomes. The methods involve stably integrating into the genome of a plant one or more primary, secondary, tertiary and quaternary nucleotide constructs comprising coding sequences for an enzyme involved in PHA synthesis in a plant. The primary nucleotide construct comprises a coding sequence for an enzyme that catalyzes the synthesis of R-(−)-3-hydroxyacyl-CoA, wherein at least one such construct comprises a nucleotide sequence encoding an OAR enzyme of the invention. The secondary nucleotide construct comprises a coding sequence for a 3-ketoacyl-CoA reductase. The tertiary nucleotide construct comprises a coding sequence for a PHA synthase that is capable of catalyzing the synthesis of PHA copolymers. The quaternary nucleotide construct comprises a coding sequence for an acetyl-CoA:acetyl transferase. If desired, an additional nucleotide construct may also be stably integrated into the genome of the plant. The additional nucleotide construct comprises a nucleotide sequence encoding a NADH kinase or an NAD kinase.

Nucleotide constructs that can be utilized in this third embodiment include the nucleotide constructs of the first and second embodiments, described supra. The nucleotide constructs used in this third embodiment, each additionally comprises an operably linked promoter and, if necessary, an operably linked peroxisome-targeting signal to direct the encoded protein to the peroxisome. By targeting such enzymes to the peroxisome, the plant is capable of increased synthesis of intermediate molecules, particularly intermediate molecules that are substrates for a PHA synthase that catalyzes the formation of copolymers.

It is recognized that the methods of the present invention can be used in combination with methods for producing PHA homopolymers, copolymers or both. Further, it is recognized that it may be necessary to lower or eliminate the activity of an endogenous enzyme in a plant that in some way limits the synthesis of the desired intermediate molecule. Such an endogenous enzyme may, for example, catabolize or modify the intermediate molecule in an undesirable way. Methods for lowering or eliminating the activity of an enzyme in a plant include sense and antisense suppression methods.

The OAR sequences of the invention are provided in expression cassettes for expression in the plant of interest. The cassette will include 5' and 3' regulatory sequences operably linked to an OAR sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case of protein coding sequences, "operably linked" includes joining two protein coding sequences in such a manner that both sequences are in the same reading frame for translation. For example, a nucleotide sequence encoding a peroxisome-targeting signal may be joined to the 3' end of a coding sequence of a protein of the invention in such manner that both sequences are in the same reading frame for translation to yield a the protein of the invention with a C-terminal addition of the peroxisome-targeting signal. The cassette may additionally contain at least one additional gene to be cotransformed into the organism. Alternatively, the additional gene(s) can be provided on multiple expression cassettes.

Such an expression cassette is provided with a plurality of restriction sites for insertion of an OAR sequence to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 1 7:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 1 7:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters may be selected based on the desired timing, localization and level of expression genes encoding enzymes in a plant. Constitutive, seed-preferred, germination-preferred, tissue-preferred and chemical-regulatable promoters can be used in the practice of the invention.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

The methods of the invention are useful for producing PHA in seeds. To drive the expression of an OAR nucleotide sequence of the invention in seeds, seed preferred promoters can be operably linked to an OAR nucleotide sequence. "Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

For tissue-preferred expression, the coding sequences of the invention can be operably linked to tissue-preferred promoters. For example, leaf-preferred promoters may be utilized if expression in leaves is desired. Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Other tissue-preferred promoters include, for example, Kawamata et al. (1997) *Plant Cell Physiol.* 38(7):792-803; Hansen et al. (1997) *Mol Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Lam (1994) *Results Probl Cell Differ.* 20:181-196; Orozco et al. (1993) *Plant Mol Biol.* 23(6):1129-1138; and Guevara-Garcia et al. (1993) *Plant J.* 4(3):495-505.

In the practice of the invention, it may be desirable to use chemical-regulatable promoters to control the expression of gene in a plant. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulatable promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

In particular embodiments of the invention, the expression cassette may additionally comprise a nucleotide sequence encoding a peroxisome-targeting signal, in order to direct an OAR to the peroxisomes of a plant. Methods for directing an enzyme to the peroxisome are well known in the art. Typically, such methods involve operably linking a nucleotide sequence encoding a peroxisome-targeting signal to the coding sequence of a protein or modifying the coding sequence to additionally encode the peroxisome-targeting signal without substantially affecting the intended function of the encoded protein. See, for example, Olsen et al. (1993) *Plant Cell* 5:941-952, Mullen et al. (1997) *Plant Physiol.* 115:881-889, Gould et al. (1990) *EMBO J.* 9:85-90, Flynn et al. (1998) *Plant J.* 16:709-720, Preisig-Muller and Kindl (1993) *Plant Mol. Biol.* 22:59-66, and Kato et al. (1996) *Plant Cell* 8:1601-1611; herein incorporated by reference. In one embodiment, the peroxisome-targeting signal is a PTS 1-type peroxisomal targeting signal.

It is recognized that an OAR of the invention may be directed to the peroxisome by operably linking a peroxisome-targeting signal to the C-terminus or the N-terminus of the enzyme. It is further recognized that an enzyme which is synthesized with a peroxisome-targeting signal may be processed proteolytically in vivo resulting in the removal of the peroxisome-targeting signal from the amino acid sequence of the mature, peroxisome-localized enzyme.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324-3328; Murray et al. (1989) *Nucleic Acid Research* 17:477-498; and WO 91/16432.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed.

Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In the methods of the present invention, plants genetically manipulated to produce PHA are utilized. By "genetically manipulated" is intended modifying the genome of an organism, preferably a plant, including cells and tissue thereof, by any means known to those skilled in the art. Modifications to a genome include both losses and additions of genetic material as well as any sorts of rearrangements in the organization of the genome. Such modifications can be accomplished by, for example, transforming a plant's genome with a nucleotide construct containing nucleotide sequences which are native to the recipient plant, non-native or a combination of both, conducting a directed sexual mating or cross pollination within a single species or between related species, fusing or transferring nuclei, inducing mutagenesis and the like.

In the practice of certain specific embodiments of the present invention, a plant is genetically manipulated to produce more than one heterologous enzyme involved in PHA synthesis. Those of ordinary skill in the art realize that this can be accomplished in any one of a number of ways. For example, each of the respective coding sequences for such enzymes can be operably linked to a promoter and then joined together in a single continuous polynucleotide fragment comprising a multigenic expression cassette. Such a multigenic expression cassette can be used to transform a plant to produce the desired outcome. Alternatively, separate plants can be transformed with expression cassettes containing one or a subset of the desired set of coding sequences. Transformed plants that express the desired activity can be selected by standard methods available in the art such as, for example, assaying enzyme activities, immunoblotting using antibodies which bind to the enzymes of interest, assaying for the products of a reporter or marker gene, and the like. Then, all of the desired coding sequences can be brought together into a single plant through one or more rounds of cross pollination utilizing the previously selected transformed plants as parents.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described supra for selecting transformed plants. If necessary, the selected progeny can be used as either the pollen donor or pollen recipient in a subsequent cross pollination.

The invention can be practiced with any plant. Plants of interest include, but are not limited to, corn (*Zea mays*), canola and other *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, pomes and soft fruit (apples, pears, plums, peaches, almonds, cherries), ornamentals, and conifers. In an embodiment of the invention, oilseed plants are transformed with the OAR nucleotide sequences of the invention. Such oilseed plants include, but are not limited to canola, sunflower, safflower, soybean, peanut, cotton, flax, coconut and oil palm.

Additionally, the OAR nucleotide sequences of the invention may be used in methods for producing PHA in non-human host organisms other than plants; including but not limited to bacteria, yeasts, and fungi. Useful host organisms for PHA production include *Actinomycetes* (e.g., *Streptomyces* sp. and *Nocardia* sp.); bacteria (e.g., *Ralstonia* (e.g., *R. eutropha*), *Bacillus cereus*, *B. subtilis*, *B. licheniformis*, *B. megaterium*, *Escherichia coli*, *Klebsiella* (e.g., *K. aerogenes* and *K. oxytoca*), *Lactobacillus*, *Methylomonas*, *Pseudomonas* (e.g., *P. putida* and *P. fluorescens*); fungi (e.g., *Aspergillus, Cephalosporium*, and *Penicillium*); and yeast (e.g., *Saccharomyces, Rhodotorula, Candida, Hansenula*, and *Pichia*).

The following examples are offered by way of illustration and not by way of limitation.

EXAMPLES

Example 1

Isolation of Maize and Soybean OAR Genes

The dehydrogenase domain of rat multifunctional protein type 2 (MFP2), were used as a query to initially identify maize OARs. Subsequently, two OAR cDNAs (ESTs) from maize (maize OAR1 and OAR2), and two OAR cDNAs (ESTs) from soybean (soybean OAR1 and OAR2) were identified. The corresponding cDNAs were isolated by known methods. The nucleic acid sequences for these cDNAs, and the polypeptides encoded thereby, are set forth in SEQ ID Nos:1-4 for the maize OARs, and SEQ ID Nos: 5-8 for the soybean OARs. Sequence analysis indicates the presence of putative N-terminal transit peptide for each gene. The two transit peptides from the two soybean OARs are significantly different in length and amino acid composition, and may represent targeting signals for different organelles.

The amino acid sequences for the maize and soybean polypeptides have about 60% identity with an OAR sequence from *Cuphea lanceolata* (EMBL accession number X64566). They also share significant homology with the dehydrogenase portion of mammalian and yeast D-specific peroxisomal multifunctional proteins (MFP2) that are involved in the β-oxidation of fatty acids (Hashimoto, T. (1999) *Neurochem. Res.* 24(4): 551-63).

Example 2

Production of Transgenic Dicotyledonous Soybean Plants via Biolistic Transformation For constitutive expression of the nucleic acids of the invention, constructs comprising the SCP1 promoter (U.S. Pat. No. 6,072,050) and the OAR coding regions of the invention are introduced into embryogenic suspension cultures of soybean, or other dicots, by particle bombardment using essentially the methods described in Parrott et al. (1989) *Plant Cell Rep.* 7: 615-617. For seed-preferred expression, constructs comprising the beta phaseolin promoter (van der Geest (1996) *Plant Mol Biol.* 32(4): 579-88; Slightom et al. (1983) *Proc. Natl. Acad Sci USA* 80: 1897-1901) and the OAR coding regions of the invention are used for the particle bombardment.

Seed is removed from pods when the cotyledons are between 3 and 5 mm in length. The seeds are sterilized in a Clorox bleach solution (0.5%) for 15 minutes after which time the seeds are rinsed with sterile distilled water. The immature cotyledons are excised by first cutting away the portion of the seed that contains the embryo axis. The cotyledons are then removed from the seed coat by gently pushing the distal end of the seed with the blunt end of the scalpel blade. The cotyledons are then placed (flat side up) on SB1 initiation medium (MS salts, B5 vitamins, 20 mg/L 2,4-D, 31.5 g/l sucrose, 8 g/L TC Agar, pH 5.8). The Petri plates are incubated in the light (16 hour day; 75-80 µE at 26° C. After 4 weeks of incubation the cotyledons are transferred to fresh SB1 medium. After an additional two weeks, globular stage somatic embryos that exhibit proliferative areas are excised and transferred to FN Lite liquid medium (Samoylov et al. (1998) *In Vitro Cell Dev. Biol.—Plant* 34:8-13). About 10 to 12 small clusters of somatic embryos are placed in 250 ml flasks containing 35 ml of SB172 medium.

The embryogenic suspension cultures are maintained in 35 mL liquid media on a rotary shaker, 150 rpm, at 26° C. with florescent lights (20 µE on a 16:8 hour day/night schedule. Cultures are sub-cultured every two weeks by inoculating approximately 35 mg of tissue into 35 mL of liquid medium.

Embryogenic suspension cultures are then transformed using particle gun bombardment (Klein et al. (1987) *Nature* (London) 327:70, U.S. Pat. No. 4,945,050). A BioRad Biolistic™ PDS 1000/HE instrument is used for these transformations. A selectable marker gene which can be used to facilitate transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is agitated for three minutes, spun in a microfuge for 10 seconds and the supernatant removed. The DNA-coated particles are washed once in 400 µL 70% ethanol and resuspended in 40 µL of anhydrous ethanol. The DNA/particle suspension is sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. Membrane rupture pressure is set at 1100 psi and the chamber is evacuated to a vacuum of 28 inches mercury. The tissue is placed approximately 8 cm away from the retaining screen, and is bombarded three times. Following bombardment, the tissue is divided in half and placed back into 35 ml of FN Lite medium.

Five to seven days after bombardment, the liquid medium is exchanged with fresh medium. Eleven days post-bombardment the medium is exchanged with fresh medium containing 50 mg/mL hygromycin. This selective medium is refreshed weekly. Seven to eight weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos, or tissue is regenerated into whole plants by maturation and germination of individual embryos. Tissue from the regenerated plant is tested for OAR expression using known methods for detecting gene expression; such as Western and Northern Blotting. Active expression of the OAR protein is tested by assaying for acetoacetyl-CoA- and/or acetoacetyl-ACP reductase activity. Such assay methods are known in the art. See, for example, Shimakata et al. (1982) *Arch. Biochem. Biophys.* 218(1): 77.

Alternatively, an *Agrobacterium* transformation method is used, for example, as described in Byrne et al. (1987) *Plant Cell Tissue and Organ Culture* 8:3-15; Facciotti et al. (1985) *Biotechnology* (New York) 3:241; or U.S. Pat. No. 5,569, 834.

Example 3

Transformation and Regeneration of Transgenic Maize Plants by Particle Bombardment For constitutive expression of an OAR nucleotide sequence of the invention, immature maize embryos from greenhouse donor plants are bombarded with a plasmid containing a constitutive promoter operably linked to an OAR nucleotide sequence of the invention and the selectable marker gene PAT (Wohlleben et al. (1988) *Gene* 70:25-37), which confers resistance to the herbicide Bialaphos. For seed-preferred expression of an OAR nucleotide sequence of the invention, immature maize embryos from greenhouse donor plants are bombarded with a plasmid containing a seed-preferred promoter operably linked to an OAR nucleotide sequence of the invention and the selectable marker gene PAT. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising an OAR nucleotide sequence of the invention operably linked to a constitutive or seed-preferred promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for OAR expression, for example.

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 4

Production of Transgenic Maize Plants via Agrobacterium-Mediated Transformation For *Agrobacterium*-mediated transformation of maize an OAR nucleotide sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the OAR nucleotide sequence of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 5

Production of PHA Copolymers in Plants

Transgenic plants expressing one or more OAR enzymes of the invention are produced according to the methods illustrated in Examples 2-4, or by any other method for producing transgenic plants that is known in the art. Additionally, the plants are also transformed with, and express a PHA synthase, particularly a PHA synthase capable of accepting $C_4$-$C_{18}$ substrates. While such a PHA synthase will typically be capable of using monomers of 3-hydroxy-alkanoic acids-CoAs with hydroxyalkanoate carbon chain lengths of $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$, and invention does not depend on a particular PHA synthase being capable of utilizing all monomers with the range of $C_4$-$C_{18}$. Furthermore, the invention encompasses the use of PHA synthases that do not utilize monomer all carbon chain lengths from $C_4$-$C_{18}$. Alternatively, the plants are transformed with a PHB synthase, as well as a PHA synthase capable of accepting substrate longer than $C_4$ PHA copolymer production is tested by methods known in the art. For example, see Mittendorf et al. (1998) *Proc. Natl. Acad. Sci. USA* 95:13397-13402.

If desired, the plants can also be transformed as described supra with nucleotide sequences encoding additional enzymes that are necessary for, or favorably affect, the synthesis of PHA in the plants. Such enzymes include, for example, one or more PHA synthases. The OAR enzymes, and any other desired enzymes, can be targeted in the plant to the peroxisomes by operably linking a peroxisome-targeting sequence to a sequence encoding the enzyme.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
   (a) a nucleotide sequence comprising the nucleotide sequence set forth in SEQ ID NO: 5 or 7;
   (b) a nucleotide sequence which encodes a polypeptide having the amino acid sequence set forth in SEQ ID NO: 6 or 8;
   (c) a nucleotide sequence having at least 90% nucleotide sequence identity to the nucleotide sequence set forth in SEQ ID NO: 5 or 7, wherein said nucleotide sequence encodes a polypeptide having 3-oxoacyl-[acyl carrier protein] reductase (OAR) activity;
   (d) a nucleotide sequence which encodes a polypeptide having at least 90% amino acid sequence identity to the amino acid sequence set forth in SEQ ID NO: 6 or 8, wherein said polypeptide has OAR activity; and
   (e) a nucleotide sequence fully complementary to a nucleotide sequence of (a), (b), (c), or (d).

2. The nucleic acid molecule of claim 1, wherein said nucleotide sequence identity is at least 95%, and wherein said nucleotide sequence encodes a polypeptide having OAR activity.

3. The nucleic acid molecule of claim 1, wherein said amino acid sequence identity is at least 95%, and wherein said polypeptide has OAR activity.

4. An expression cassette comprising at least one nucleic acid molecule of claim 1 operably linked to a promoter.

5. The expression cassette of claim 4, wherein said promoter drives expression in a plant cell.

6. The expression cassette of claim 5 further comprising a peroxisome-targeting signal operably linked to said nucleic acid molecule.

7. A non-human host cell transformed with at least one expression cassette of claim 4.

8. The host cell of claim 7, wherein said host cell is selected from the group consisting of a plant cell, a bacterial cell, and a yeast cell.

9. A transgenic plant comprising in its genome a stably integrated nucleotide construct comprising a nucleic acid molecule operably linked to a promoter that drives expression in a plant cell, wherein said nucleic acid molecule comprises a nucleotide sequence selected from the group consisting of:
   (a) a nucleotide sequence comprising the nucleotide sequence set forth in SEQ ID NO: 5 or 7;
   (b) a nucleotide sequence which encodes a polypeptide having the amino acid sequence set forth in SEQ ID NO: 6 or 8;
   (c) a nucleotide sequence having at least 90% nucleotide sequence identity to the nucleotide sequence set forth in SEQ ID NO: 5 or 7, wherein said nucleotide sequence encodes a polypeptide has OAR activity;
   (d) a nucleotide sequence which encodes a polypeptide having at least 90% amino acid sequence identity to the amino acid sequence set forth in SEQ ID NO: 6 or 8, wherein said polypeptide comprises OAR activity; and
   (e) a nucleotide sequence fully complementary to a nucleotide sequence of (a), (b), (c), or (d).

10. The plant of claim 9, wherein said promoter is a selected from the group consisting of a constitutive promoter, a seed-preferred promoter, a chemical-regulatable promoter, a germination-preferred promoter, and a leaf-preferred promoter.

11. The plant of claim 9, wherein said plant is a monocot.

12. The plant of claim 11, wherein said monocot is selected from the group consisting of corn, wheat, rice, barley, millet, sorghum, rye, oats, banana, coconut, and oil palm.

13. The plant of claim 9, wherein said plant is a dicot.

14. The plant of claim 13, wherein said dicot is selected from the group consisting of soybean, alfalfa, flax, sunflower, safflower, canola, *Brassica* spp., peanut, and cotton.

15. Transformed seed of the plant of claim 9.

16. Transformed seed of the plant of claim 10.

17. Transformed seed of the plant of claim 12.

18. Transformed seed of the plant of claim 14.

19. A transformed plant cell comprising in its genome a stably integrated nucleotide construct comprising a nucleic acid molecule operably linked to a promoter that drives expression in a plant cell, wherein said nucleic acid molecule comprises a nucleotide sequence selected from the group consisting of:
   (a) a nucleotide sequence comprising the nucleotide sequence set forth in SEQ ID NO: 5 or7;
   (b) a nucleotide sequence which encodes a polypeptide having the amino acid sequence set forth in SEQ ID NO: 6 or 8;
   (c) a nucleotide sequence having at least 90% nucleotide sequence identity to the nucleotide sequence set forth in SEQ ID NO: 5 or 7, wherein said nucleotide sequence encodes a polypeptide comprising OAR activity;
   (d) a nucleotide sequence which encodes a polypeptide having at least 90% amino acid sequence identity to the amino acid sequence set forth in SEQ ID NO: 6 or 8, wherein said polypeptide has OAR activity; and
   (e) a nucleotide sequence fully complementary to a nucleotide sequence of (a), (b), (c), or (d).

* * * * *